(12) United States Patent
Park et al.

(10) Patent No.: US 12,104,104 B2
(45) Date of Patent: Oct. 1, 2024

(54) PHOSPHOR MONOMOLECULAR COMPOUND, ORGANIC TRANSISTOR USING SAME, AND WATER DECOMPOSITION AND HYDROGEN PRODUCTION PHOTOCATALYTIC SYSTEM USING SAME

(71) Applicant: SEOUL NATIONAL UNIVERSITY R&DB FOUNDATION, Seoul (KR)

(72) Inventors: Soo Young Park, Seoul (KR); Min Woo Choi, Seoul (KR); Jin Hong Kim, Busan (KR); Won Sik Yoon, Gyeonggi-do (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 987 days.

(21) Appl. No.: 17/048,654

(22) PCT Filed: Apr. 4, 2019

(86) PCT No.: PCT/KR2019/003987
§ 371 (c)(1),
(2) Date: Oct. 19, 2020

(87) PCT Pub. No.: WO2019/203481
PCT Pub. Date: Oct. 24, 2019

(65) Prior Publication Data
US 2021/0179933 A1 Jun. 17, 2021

(30) Foreign Application Priority Data

Apr. 19, 2018 (KR) .................. 10-2018-0045675

(51) Int. Cl.
*C07D 471/04* (2006.01)
*C01B 3/04* (2006.01)
(Continued)

(52) U.S. Cl.
CPC .............. *C09K 11/06* (2013.01); *C01B 3/042* (2013.01); *C07D 471/04* (2013.01);
(Continued)

(58) Field of Classification Search
CPC .................................................... C07D 471/04
See application file for complete search history.

(56) References Cited

FOREIGN PATENT DOCUMENTS

| KR | 10-2015-0023515 | * | 3/2015 | ........... C07D 471/04 |
|---|---|---|---|---|
| WO | 2013/182262 | | 12/2013 | |
| WO | 2017/133752 | | 8/2017 | |

OTHER PUBLICATIONS

Yoon, W. S., Macromolecules, 2016, 49, pp. 8489-8497, Published Nov. 3, 2016.
(Continued)

*Primary Examiner* — Caixia Lu
(74) *Attorney, Agent, or Firm* — Bridgeway IP Law Group, PLLC; Sang Ho Lee; Hyun Woo Shin

(57) ABSTRACT

The present invention relates to a phosphor monomolecular compound, an organic transistor using same, and a water splitting and hydrogen production photocatalytic system using same. More specifically, the present invention comprises a water-soluble monomolecular compound including 1,5-naphtyridine-2,6-dione structure as a phosphor monomolecular compound.

9 Claims, 10 Drawing Sheets

(51) Int. Cl.
  *C09K 11/06* (2006.01)
  *H10K 10/46* (2023.01)
  *H10K 10/82* (2023.01)
  *H10K 85/60* (2023.01)
  *H10K 50/15* (2023.01)
  *H10K 50/30* (2023.01)

(52) U.S. Cl.
  CPC ........... *H10K 10/462* (2023.02); *H10K 10/82* (2023.02); *H10K 85/6572* (2023.02); *C01B 2203/0277* (2013.01); *C01B 2203/1041* (2013.01); *C09K 2211/1022* (2013.01); *H10K 50/15* (2023.02); *H10K 50/30* (2023.02)

(56) References Cited

OTHER PUBLICATIONS

Fu, C., Chem. Mater., 2017, pp. 2979-2987, Published Feb. 24, 2017.
Yoon, W. S., Adv. Energy Mater. 2018, 8, 1701467, 1-10.
Choi, M. W. In: Frontiers of Organic Semiconductor Lasers 2018, Guangzhou, 2018, 1-7.
Kim, J. H., ACS Appl. Mater. Interfaces, Jan. 30, 2019, 8301-8309.

\* cited by examiner

PHOSPHOR MONOMOLECULAR COMPOUND, ORGANIC TRANSISTOR USING SAME, AND WATER DECOMPOSITION AND HYDROGEN PRODUCTION PHOTOCATALYTIC SYSTEM USING SAME

TECHNICAL FIELD

The present invention relates to a phosphor monomolecular compound, an organic transistor using the same, and a water splitting and hydrogen production photocatalytic system using the same, and more particularly, to a novel phosphor monomolecular compound including a 1,5-naphthyridine-2,6-dione structure, an organic transistor and a water splitting and hydrogen production photocatalytic system with increased efficiency by using the same.

BACKGROUND ART

Organic phosphors are inexpensive and may be synthesized via various pathways. Also, it is advantageous that they are synthesized and used according to their purposes for use by introducing various substituents. Extensive research has been conducted on organic phosphors having such advantages in the fields of biotechnology such as bio sensors, bio imaging, and cell monitoring and light-emitting devices such as organic light-emitting diodes (OLEDs) and organic light-emitting transistors (OLETs). Representatively, various organic phosphors such as Fluorecein, Anthracene, Coumarin, and BODIPY have been developed and commercially available, and thus applied in various fields.

Phosphors used in OLEDs or OLETs are required to emit light of a desired wavelength, and phosphors used in the biotechnology are required to be water-soluble. However, there may be problems such as difficulty in controlling a molecular structure of the organic phosphor in order to emit light of a desired wavelength or low photoluminescent efficiency. Particularly, the organic phosphor has hydrophobicity that is difficult to be applied to the biotechnology.

DESCRIPTION OF EMBODIMENTS

Technical Problem

The present invention has been proposed to solve various problems including the above problems, and an object of the present invention is to provide a water-soluble monomolecular compound including a 1,5-naphthyridine-2,6-dione structure as a phosphor capable of emitting light of a wide wavelengths and having a high photoluminescent efficiency.

Also, the present invention provides an organic transistor and a water splitting and hydrogen production photocatalytic system having enhanced performance by using the monomolecular compound.

However, these problems to be solved are illustrative and the scope of the present invention is not limited thereby.

Solution to Problem

According to an aspect of the present disclosure to solve the above problems, provided is a phosphor monomolecular compound represented by Chemical Structural Formula 1 below.

[Chemical Structural Formula 1]

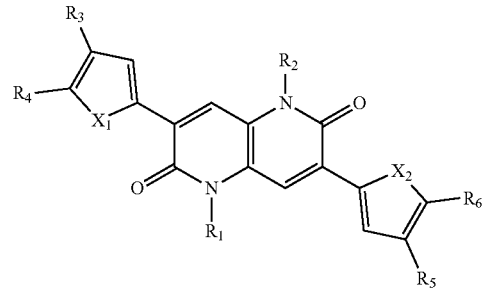

In Chemical Structural Formula 1 above,
the $X_1$ and $X_2$ are each independently O, S, Se, NH, or NR', and
the $R_1$, $R_2$, $R_3$, $R_4$, $R_5$, and $R_6$ are each independently H, F, Cl, Br, I, a C1-C50 alkyl group, a C6-C50 aryl group, —COOR', —(CH$_2$CH$_2$O)$_n$CH$_3$, or NR'$_2$,
wherein the R's are each independently a C1-C50 alkyl group or a C6-C50 aryl group, and
the n is an integer from 1 to 50.

According to another aspect of the present disclosure to solve the above problems, provided is a phosphor monomolecular compound represented by

[Chemical Structural Formula 2]

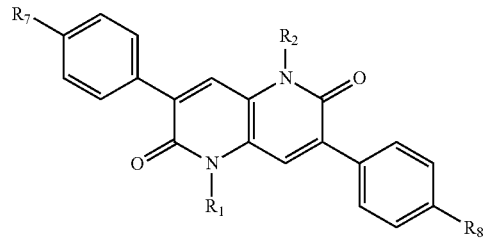

In Chemical Structural Formula 2 above,
the $R_1$, $R_2$, $R_7$, and $R_8$ are each independently H, F, Cl, Br, I, a C1-C50 alkyl group, a C6-C50 aryl group, —COOR', —(CH$_2$CH$_2$O)$_n$CH$_3$, or NR'$_2$,
wherein the R's are each independently a C1-C50 alkyl group or a C6-C50 aryl group, and
the n is an integer from 1 to 50.

According to another aspect of the present disclosure to solve the above problems, provided is a phosphor monomolecular compound represented by Chemical Structural Formula 3 below.

[Chemical Structural Formula 3]

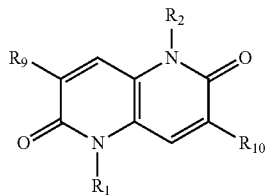

In Chemical Structural Formula 3 above,
the $R_1$ and $R_2$ are each independently H, F, Cl, Br, I, a C1-C50 alkyl group, a C6-C50 aryl group, —COOR', —(CH$_2$CH$_2$O)$_n$CH$_3$, or NR'$_2$, and the $R_9$ and $R_{10}$ are each independently naphthalene

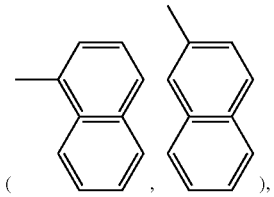

pyridine

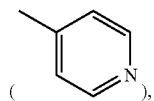

or furan

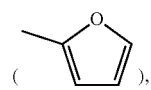

wherein the R's are each independently a C1-C50 alkyl group or a C6-C50 aryl group, and the n is an integer from 1 to 50.

In addition, according to an embodiment of the present invention, in Chemical Structural Formula 1 above, the $R_1$, $R_2$, $R_3$, $R_4$, $R_5$, $R_6$, and R' may be each independently a C1-C26 alkyl group or a C6-C32 aryl group.

In addition, according to an embodiment of the present invention, in Chemical Structural Formula 2 above, the $R_1$, $R_2$, $R_7$, $R_8$, and R' may be each independently a C1-C26 alkyl group or a C6-C32 aryl group.

In addition, according to an embodiment of the present invention, in Chemical Structural Formula 3 above, the $R_1$, $R_2$ and R' may be each independently a C1-C26 alkyl group or a C6-C32 aryl group.

In addition, according to an embodiment of the present invention, the $R_1$ and $R_2$ may be each independently a C5-C14 alkyl group.

In addition, according to an embodiment of the present invention, in Chemical Structural Formula 1 above, the $R_3$, $R_4$, $R_5$, and $R_6$ may be each independently a C9-C22 alkyl group.

In addition, according to an embodiment of the present invention, in Chemical Structural Formula 2 above, the $R_7$ and $R_8$ may be each independently a C9-C22 alkyl group.

According to another aspect of the present disclosure to solve the above problems, provided is an organic transistor including a substrate, a gate electrode formed on the substrate, an insulating layer formed on the gate electrode, a hole transport layer formed on the insulating layer, and a source electrode and a drain electrode both formed on the hole transport layer, wherein the hole transport layer includes a phosphor monomolecular compound represented by any one of Chemical Structural Formulae 1 to 3 below.

[Chemical Structural Formula 1]

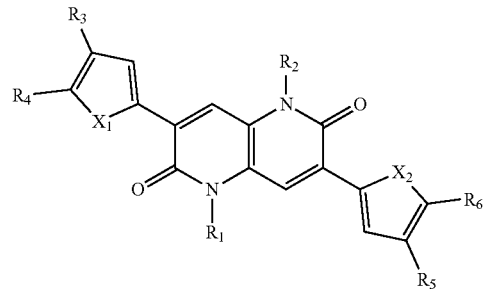

In Chemical Structural Formula 1 above, the $X_1$ and $X_2$ are each independently O, S, Se, NH, or NR', and the $R_1$, $R_2$, $R_3$, $R_4$, $R_5$, and $R_6$ are each independently H, F, Cl, Br, I, a C1-C50 alkyl group, a C6-C50 aryl group, —COOR', —(CH$_2$CH$_2$O)$_n$CH$_3$, or NR'$_2$, wherein the R's are each independently a C1-C50 alkyl group or a C6-C50 aryl group, and the n is an integer from 1 to 50.

According to another aspect of the present disclosure to solve the above problems, provided is a phosphor monomolecular compound represented by Chemical Structural Formula 2 below.

[Chemical Structural Formula 2]

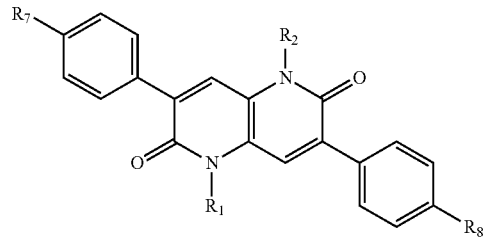

In Chemical Structural Formula 2 above, the $R_1$, $R_2$, $R_7$ and $R_8$ are each independently H, F, Cl, Br, I, a C1-C50 alkyl group, a C6-C50 aryl group, —COOR', —(CH$_2$CH$_2$O)$_n$CH$_3$, or NR'$_2$, wherein the R's are each independently a C1-C50 alkyl group or a C6-C50 aryl group, and the n is an integer from 1 to 50.

According to another aspect of the present disclosure to solve the above problems, provided is a phosphor monomolecular compound represented by Chemical Structural Formula 3 below.

[Chemical Structural Formula 3]

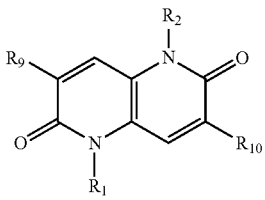

In Chemical Structural Formula 3 above,
the $R_1$ and $R_2$ are each independently H, F, Cl, Br, I, a C1-C50 alkyl group, a C6-C50 aryl group, —COOR', —$(CH_2CH_2O)_nCH_3$, or $NR'_2$, and
the $R_9$ and $R_{10}$ are each independently naphthalene

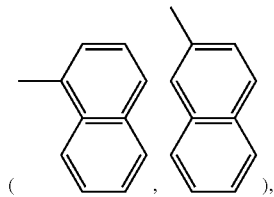

pyridine

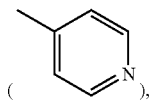

or furan

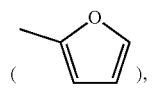

wherein the R's are each independently a C1-C50 alkyl group or a C6-C50 aryl group, and
the n is an integer from 1 to 50.

According to another aspect of the present disclosure to solve the above problems, provided is a water splitting and hydrogen production photocatalytic system including a photocatalyst in an aqueous solution, wherein the photocatalyst includes a phosphor monomolecular compound represented by any one of Chemical Structural Formulae 1 to 3.

[Chemical Structural Formula 1]

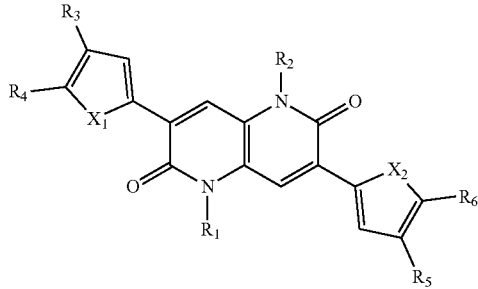

In Chemical Structural Formula 1 above,
the $X_1$ and $X_2$ are each independently O, S, Se, NH, or NR', and
the $R_1$, $R_2$, $R_3$, $R_4$, $R_5$, and $R_6$ are each independently H, F, Cl, Br, I, a C1-C50 alkyl group, a C6-C50 aryl group, —COOR', —$(CH_2CH_2O)_nCH_3$, or $NR'_2$,
wherein the R's are each independently a C1-C50 alkyl group or a C6-C50 aryl group, and
the n is an integer from 1 to 50.

According to another aspect of the present disclosure to solve the above problems, provided is a phosphor monomolecular compound represented by Chemical Structural Formula 2 below.

[Chemical Structural Formula 2]

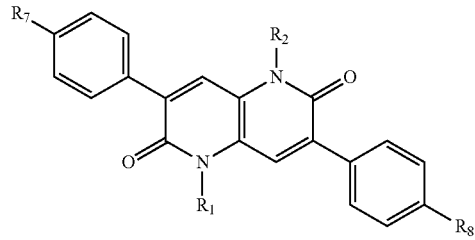

In Chemical Structural Formula 2 above,
the $R_1$, $R_2$, $R_7$ and $R_8$ are each independently H, F, Cl, Br, I, a C1-C50 alkyl group, a C6-C50 aryl group, —COOR', —$(CH_2CH_2O)_nCH_3$, or $NR'_2$,
wherein the R's are each independently a C1-C50 alkyl group or a C6-C50 aryl group, and
the n is an integer from 1 to 50.

According to another aspect of the present disclosure to solve the above problems, provided is a phosphor monomolecular compound represented by Chemical Structural Formula 3 below.

[Chemical Structural Formula 3]

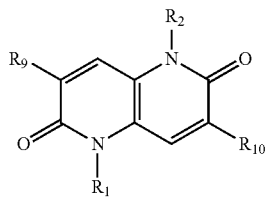

In Chemical Structural Formula 3 above,
the $R_1$ and $R_2$ are each independently H, F, Cl, Br, I, a C1-C50 alkyl group, a C6-C50 aryl group, —COOR', —$(CH_2CH_2O)_nCH_3$, or $NR'_2$, and
the $R_9$ and $R_{10}$ are each independently naphthalene

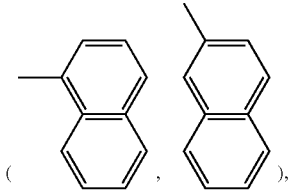

pyridine

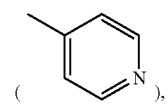

or furan

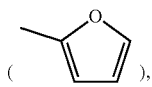

wherein the R's are each independently a C1-C50 alkyl group or a C6-C50 aryl group, and
the n is an integer from 1 to 50.

Advantageous Effects of Disclosure

According to an embodiment of the present invention as described above, a water-soluble monomolecular compound including a 1,5-naphtyridine-2,6-dione structure capable of emitting light of a wide range of wavelengths and a high photoluminescent efficiency may be provided.

Also, the present invention may improve performance of an organic transistor and a water splitting and hydrogen production photocatalytic system by using the monomolecular compound.

However, the scope of the present invention is not limited by these effects.

MODE OF DISCLOSURE

Figure 1:
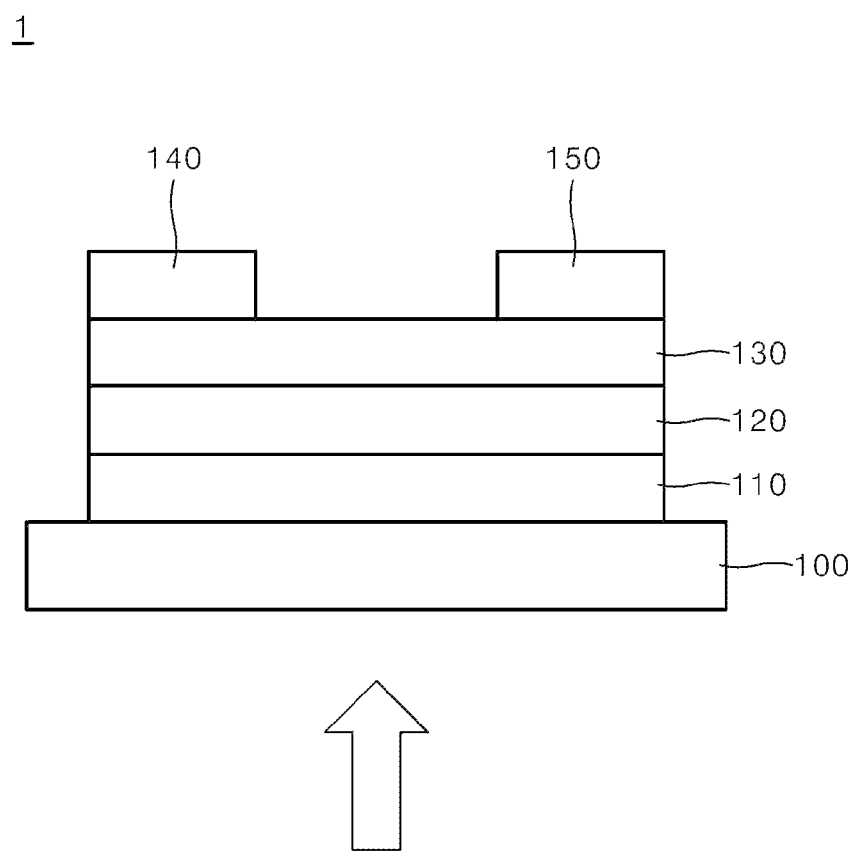
FIG. 1 is a schematic diagram illustrating a structure of an organic transistor according to an embodiment of the present invention.

In the following detailed description, reference is made to the accompanying drawings that show, by way of illustration, specific embodiments in which the invention may be practiced. These embodiments are described in sufficient detail to enable those skilled in the art to practice the invention. It is to be understood that the various embodiments of the invention, although different, are not necessarily mutually exclusive. For example, a particular feature, structure, or characteristic described herein, in connection with one embodiment, may be implemented within other embodiments without departing from the spirit and scope of the invention. In addition, it is to be understood that the location or arrangement of individual elements within each disclosed embodiment may be modified without departing from the spirit and scope of the invention. The following detailed description is, therefore, not to be taken in a limiting sense, and the scope of the present invention is defined only by the appended claims, appropriately interpreted, along with the full range of equivalents to which the claims are entitled. In the drawings, like numerals refer to the same or similar functionality throughout the several views. In the drawings, the length, area, thickness, and shape of elements may be exaggerated for clarity.

Hereinafter, embodiments of the present invention will be described in detail with reference to the accompanying drawings so that the present invention may be readily implemented by those skilled in the art.

A phosphor monomolecular compound according to the present invention has an excellent photoluminescent efficiency and may be used in an organic transistor or a water splitting and hydrogen production photocatalyst. That is, an embodiment of the present invention relates to a phosphor monomolecular compound represented by Chemical Structural Formula 1 below.

[Chemical Structural Formula 1]

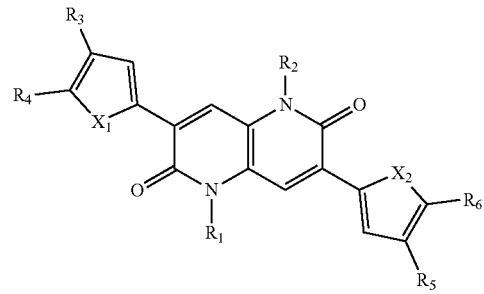

In Chemical Structural Formula 1 above,
the $X_1$ and $X_2$ are each independently O, S, Se, NH, or NR', and
the $R_1$, $R_2$, $R_3$, $R_4$, $R_5$, and $R_6$ are each independently H, F, Cl, Br, I, a C1-C50 alkyl group, a C6-C50 aryl group, —COOR', —(CH$_2$CH$_2$O)$_n$CH$_3$, or NR'$_2$,
wherein the R's are each independently a C1-C50 alkyl group or a C6-C50 aryl group, and
then is an integer from 1 to 50.

In addition, according to an embodiment of the present invention to solve the problems, provided is a phosphor monomolecular compound represented by Chemical Structural Formula 2 below.

[Chemical Structural Formula 2]

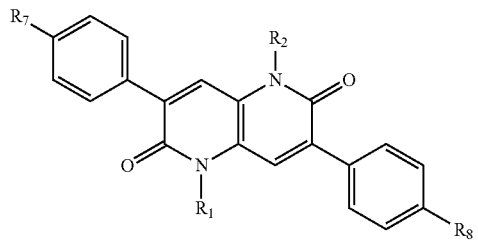

In Chemical Structural Formula 2 above,
the $R_1$, $R_2$, $R_7$, and $R_8$ are each independently H, F, Cl, Br, I, a C1-C50 alkyl group, a C6-C50 aryl group, —COOR', —(CH$_2$CH$_2$O)$_n$CH$_3$, or NR'$_2$,
wherein the R's are each independently a C1-C50 alkyl group or a C6-C50 aryl group, and
then is an integer from 1 to 50.

In addition, according to an embodiment of the present invention to solve the problems, provided is a phosphor monomolecular compound represented by Chemical Structural Formula 3 below.

[Chemical Structural Formula 3]

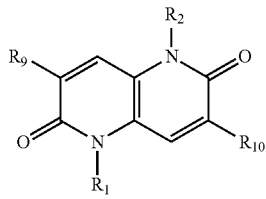

In Chemical Structural Formula 3 above,
the $R_1$ and $R_2$ are each independently H, F, Cl, Br, I, a C1-C50 alkyl group, a C6-C50 aryl group, —COOR', —(CH$_2$CH$_2$O)$_n$CH$_3$, or NR'$_2$, and
the $R_9$ and $R_{10}$ are each independently naphthalene

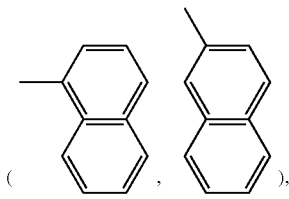

pyridine

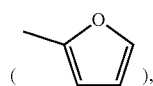

or furan

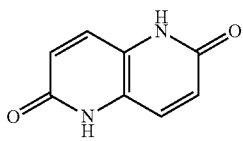

wherein the R's are each independently a C1-C50 alkyl group or a C6-C50 aryl group, and
then is an integer from 1 to 50.

As shown in Chemical Structural Formulae 1 to 3 above, the monomolecular compound according to the present invention, as a novel monomolecular compound including a 1,5-naphthyridine-2,6-dione structure, has excellent photoluminescence and water solubility due to the chemical structure as described above and have high hole mobility due to excellent crystallinity and good morphology. Thus, by using the phosphor monomolecular compound, an organic transistor having excellent photoluminescence quantum yield and high hole mobility may be manufactured.

In addition, the phosphor monomolecular compound has a high visible light absorbance and easily forms a supramolecule due to strong intermolecular attraction. In this regard, since a specific surface area may be increased by controlling the structure of the supramolecule, a water splitting and hydrogen production photocatalyst having increased catalyst efficiency may be prepared.

The monomolecular compounds represented by Chemical Structural Formulae 1 to 3 above may be prepared from 6-methoxy-1,5-naphthyridin-2(1H)-one compound represented by Chemical Formula 1 below.

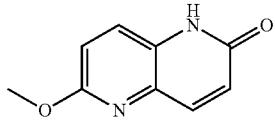

More specifically, the monomolecular compound of the present invention may be manufactured by the Stille coupling reaction of the 6-methoxy-1,5-naphthyridin-2(1H)-one compound represented by Chemical Formula 1 above, without being limited thereto.

Meanwhile, the monomolecular compound is a compound which may be prepared from 6-methoxy-1,5-naphthyridin-2(1H)-one, the methoxy group of which is not substituted, may also be prepared from 1,5-naphthyridine-2,6-dione represented by Chemical Formula 2 below.

[Chemical Formula 2]

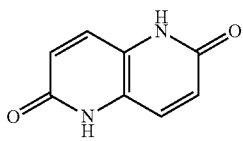

Here, the $X_1$ and $X_2$ may be each independently O, S, Se, NH, or NR', wherein R's may be each independently a C1-C26 alkyl group or a C6-C32 aryl group. In a more specific example, $X_1$ and $X_2$ may be each independently O or S.

In addition, the $R_1$, $R_2$, $R_3$, $R_4$, $R_5$, $R_6$, $R_7$, and $R_8$ may be each independently H, F, Cl, Br, I, a C1-C50 alkyl group, a C6-C50 aryl group, —COOR', —(CH$_2$CH$_2$O)$_n$CH$_3$, or NR'$_2$, wherein R's may be each independently a C1-C26 alkyl group or a C6-C32 aryl group.

In an example, the $R_1$, $R_2$, $R_3$, $R_4$, $R_5$, $R_6$, $R_7$, and $R_8$ may be each independently a C1-C46 alkyl group, a C1-C42 alkyl group, a C1-C38 alkyl group, a C1-C34 alkyl group, a C1-C30 alkyl group, a C1-C26 alkyl group, a C1-C22 alkyl group, a C6-C50 aryl group, a C6-C44 aryl group, a C6-C38 aryl group, a C6-C32 aryl group, a C6-C26 aryl group, or a C6-C20 aryl group.

In a specific example, the $R_1$, $R_2$, $R_3$, $R_4$, and R' may be each independently a C1-C26 alkyl group or a C6-C32 aryl group.

Meanwhile, the $R_1$, $R_2$, $R_3$, $R_4$, $R_5$, $R_6$, $R_7$, and $R_8$ are components that may define physical properties, such as hydrophilicity and hydrophobicity, of the monomolecular compound according to the present invention and may have an appropriate number range of carbon atoms.

In a more specific example, the $R_1$ and $R_2$ may be each independently a C5-C14 alkyl group, and the $R_3$, $R_4$, $R_5$, $R_6$, $R_7$, and $R_8$ may be each independently a C9-C22 alkyl group. Within the ranges as described above, photoluminescent efficiency and hole mobility, as a phosphor, may be controlled by adjusting physical properties of the target monomolecular compound. That is, efficiency of the organic transistor or the water splitting and hydrogen production catalyst may be increased.

Here, the n is an integer from 1 to 1,000. In a more specific example, the n may be an integer from 1 to 800, 1 to 700, 1 to 600, or 1 to 500.

As shown in Chemical Structural Formulae 1 to 3 above, the phosphor monomolecular compound according to the present invention has not only water solubility but also excellent sunlight absorbance and low driving voltage. Also, the phosphor monomolecular compound has a high hole mobility due to excellent crystallinity. In an example, the monomolecular compound may have a photoluminescence quantum yield (PLQY) of 60% or more at a maximum absorption wavelength in a wavelength range of 300 nm to 1,000 nm and a hole mobility of 0.76 cm$^2$/Vs or more.

The present invention also relates to an organic transistor including the monomolecular compound. The organic transistor may have high efficiency due to high hole mobility.

The organic transistor according to an embodiment of the present invention may include a substrate, a gate electrode formed on the substrate, an insulating layer formed on the gate electrode, a hole transport layer formed on the insulating layer, and a source electrode and a drain electrode both formed on the hole transport layer, wherein the hole transport layer may include a phosphor monomolecular compound represented by any one of Chemical Structural Formulae 1 to 3 below.

[Chemical Structural Formula 1]

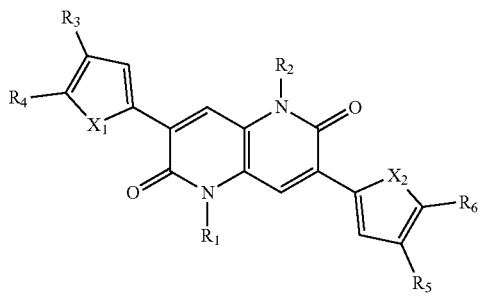

In Chemical Structural Formula 1 above, the $X_1$ and $X_2$ are each independently O, S, Se, NH, or NR', and the $R_1$, $R_2$, $R_3$, $R_4$, $R_5$, and $R_6$ are each independently H, F, Cl, Br, I, a C1-C50 alkyl group, a C6-C50 aryl group, —COOR', —(CH$_2$CH$_2$O)$_n$CH$_3$, or NR'$_2$, wherein the R's are each independently a C1-C50 alkyl group or a C6-C50 aryl group, and the n is an integer from 1 to 50.

Also, according to another embodiment of the present invention to solve the above problems, provided is a phosphor monomolecular compound represented by Chemical Structural Formula 2 below.

[Chemical Structural Formula 2]

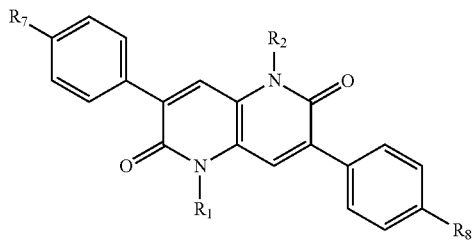

In Chemical Structural Formula 2 above, the $R_1$, $R_2$, $R_7$, and $R_8$ are each independently H, F, Cl, Br, I, a C1-C50 alkyl group, a C6-C50 aryl group, —COOR', —(CH$_2$CH$_2$O)$_n$CH$_3$, or NR'$_2$, wherein the R's are each independently a C1-C50 alkyl group or a C6-C50 aryl group, and the n is an integer from 1 to 50.

Also, according to another embodiment of the present invention to solve the above problems, provided is a phosphor monomolecular compound represented by Chemical Structural Formula 3 below.

[Chemical Structural Formula 3]

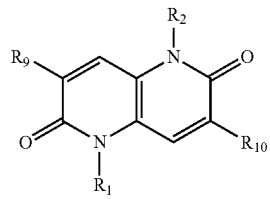

In Chemical Structural Formula 3 above, the $R_1$ and $R_2$ are each independently H, F, Cl, Br, I, a C1-C50 alkyl group, a C6-C50 aryl group, —COOR', —(CH$_2$CH$_2$O)$_n$CH$_3$, or NR'$_2$, and the $R_9$ and $R_{10}$ are each independently naphthalene

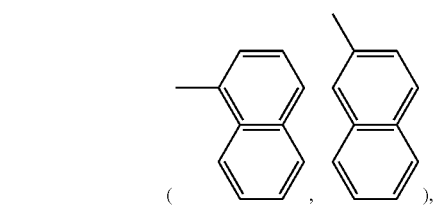

pyridine

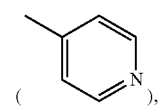

or furan

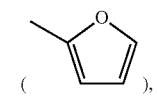

wherein the R's are each independently a C1-C50 alkyl group or a C6-C50 aryl group, and the n is an integer from 1 to 50.

The organic transistor of the present invention may include the above-described monomolecular compound represented by any one of Chemical Structural Formulae 1 to 3 as a hole transport material in a hole transport layer, thereby having high hole mobility.

FIG. 1 is a schematic diagram illustrating a structure of an organic transistor 1 according to an embodiment of the present invention.

As shown in FIG. 1, the organic transistor 1 according to the present invention may include a substrate 100, a gate electrode 110, an insulating layer 120, a hole transport layer 130, a source electrode 140, and a drain electrode 150.

The organic transistor 1 of the present invention may have a structure in which the gate electrode 110, the insulating layer 120, and the hole transport layer 130 are stacked on the substrate 100, and the source electrode 140 and the drain electrode 150 are disposed on the hole transport layer 130 to face each other as illustrated in FIG. 1. The organic transistor 1 may have a top contact-bottom gate structure in which the source electrode 140 and the drain electrode 150 are formed on the hole transport layer 130, and the gate electrode 110 is formed thereunder.

In this regard, according to an embodiment of the present invention, the hole transport layer 130 may include the phosphor monomolecular compound represented by any one of Chemical Structural Formulae 1 to 3 above.

The phosphor monomolecular compound represented by any one of Chemical Structural Formulae 1 to 3 has excellent hole mobility due to high flatness and excellent crystallinity and may realize a wide range of wavelengths due to high photoluminescent efficiency. Thus, the hole transport layer 130 may have excellent hole mobility at a low driving voltage by including the phosphor monomolecular compound represented by any one of Chemical Structural Formulae 1 to 3 described above as a hole transporting material.

In an example, the organic transistor 1 may have a hole mobility of 0.7 cm$^2$ V$^{-1}$ s$^{-1}$ or more. An upper limit of the hole mobility may be 2.76 cm$^2$ V$^{-1}$ s$^{-1}$.

Meanwhile, the present invention relates to a water splitting and hydrogen production photocatalytic system including the monomolecular compound. The water splitting and hydrogen production photocatalytic system has a high visible light absorbance and easily forms a supramolecule due to strong intermolecular attraction between catalyst molecules, thereby having excellent efficiency.

The water splitting and hydrogen production photocatalytic system according to an embodiment of the present invention includes a photocatalyst in an aqueous solution, wherein the photocatalyst includes the phosphor monomolecular compound represented by any one of Chemical Structural Formulae 1 to 3 below.

[Chemical Structural Formula 1]

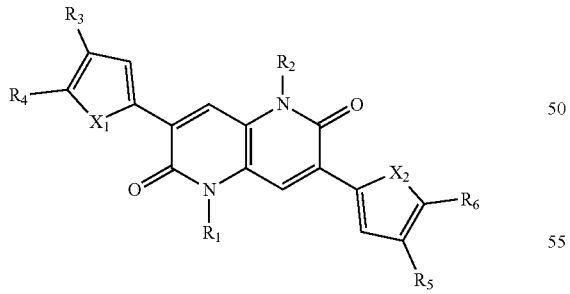

In Chemical Structural Formula 1 above,
the $X_1$ and $X_2$ are each independently O, S, Se, NH, or NR', and
the $R_1$, $R_2$, $R_3$, $R_4$, $R_5$, and $R_6$ are each independently H, F, Cl, Br, I, a C1-C50 alkyl group, a C6-C50 aryl group, —COOR', —(CH$_2$CH$_2$O)$_n$CH$_3$, or NR'$_2$,
wherein the R's are each independently a C1-C50 alkyl group or a C6-C50 aryl group, and
then is an integer from 1 to 50.

In addition, according to another embodiment of the present invention to solve the above problems, provided is a phosphor monomolecular compound represented by Chemical Structural Formula 2 below.

[Chemical Structural Formula 2]

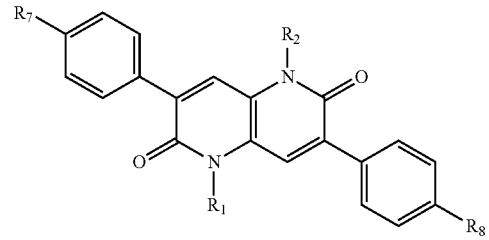

In Chemical Structural Formula 2 above,
the $R_1$, $R_2$, $R_3$, and $R_4$ are each independently H, F, Cl, Br, I, a C1-C50 alkyl group, a C6-C50 aryl group, —COOR', —(CH$_2$CH$_2$O)$_n$CH$_3$, or NR'$_2$,
wherein the R's are each independently a C1-C50 alkyl group or a C6-C50 aryl group, and
then is an integer from 1 to 50.

Also, according to another embodiment of the present invention to solve the above problems, provided is a monomolecular compound represented by Chemical Structural Formula 3 below.

[Chemical Structural Formula 3]

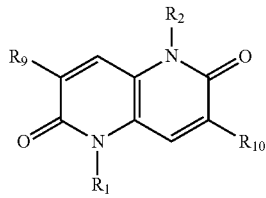

In Chemical Structural Formula 3 above,
the $R_1$ and $R_2$ are each independently H, F, Cl, Br, I, a C1-C50 alkyl group, a C6-C50 aryl group, —COOR', —(CH$_2$CH$_2$O)$_n$CH$_3$, or NR'$_2$, and
the $R_9$ and $R_{10}$ are each independently naphthalene

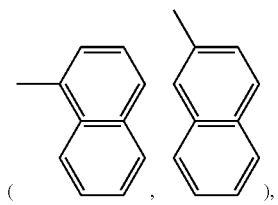

( , ), pyridine

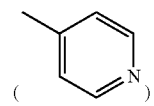

( )

or furan

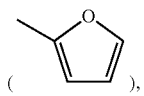

wherein the R's are each independently a C1-C50 alkyl group or a C6-C50 aryl group, and then is an integer from 1 to 50.

Figure 2:
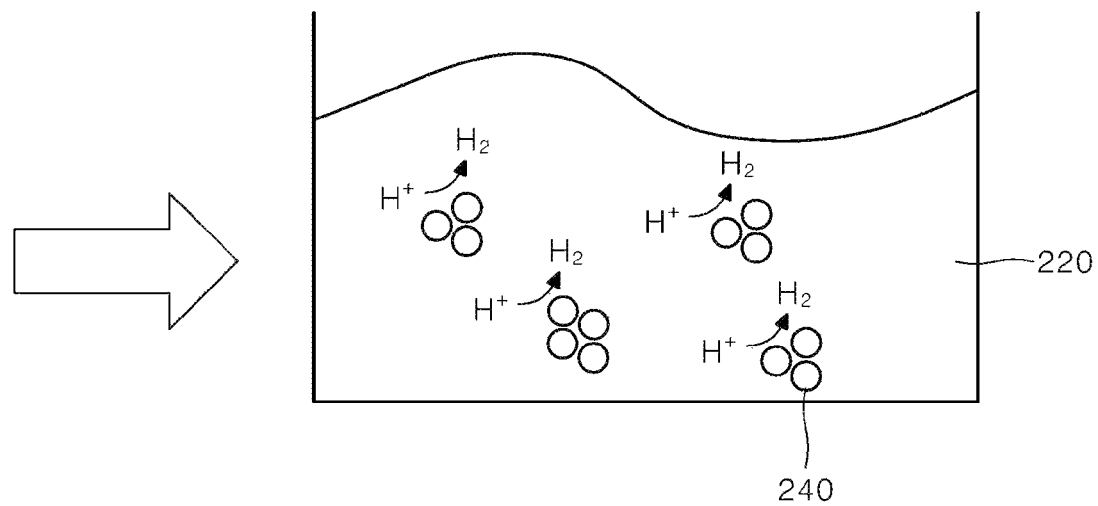
FIG. 2 is a schematic diagram illustrating a structure of a water splitting and hydrogen production photocatalytic system according to an embodiment of the present invention.

FIG. 2 is a schematic diagram illustrating a structure of a water splitting and hydrogen production photocatalytic system 2 according to the present invention.

As illustrated in FIG. 2, the water splitting and hydrogen production photocatalytic system 2 according to the present invention may include an aqueous solution 220 and a photocatalyst 240. In this regard, according to an embodiment of the present invention, the photocatalyst 240 may include the phosphor monomolecular compound represented by any one of Chemical Structural Formulae 1 to 3 above.

Referring to FIG. 2, the photocatalyst 240 in the aqueous solution 220 absorbs visible light from sunlight entering from the outside to split water ($H_2O$) into hydrogen gas ($H_2$). In this case, since the phosphor monomolecular compound has excellent visible light absorbance as described above, the water splitting and hydrogen production photocatalytic system may be manufactured by using the photocatalyst 240 including the same.

The phosphor monomolecular compound represented by any one of Chemical Structural Formulae 1 to 3 above has excellent visible light absorbance, thereby having high light absorbing efficiency. That is, the phosphor monomolecular compound has excellent catalytic activity to sunlight. In addition, the phosphor monomolecular compound represented by any one of Chemical Structural Formulae 1 to 3 above has strong intermolecular attraction, thereby forming a supramolecule. Since the specific surface area may be controlled by adjusting the structure of the supramolecule, a sufficient reaction site may be provided. That is, the water splitting and hydrogen production photocatalytic system may have increased efficiency by including the phosphor monomolecular compound represented by any one of Chemical Structural Formulae 1 to 3 above.

Hereinafter, the present invention will be described in more detail with reference to the following preparation examples and examples. However, the following examples are merely presented to exemplify the present invention, and the scope of the present invention is not limited thereto.

Preparation of Phosphor Monomolecular Compound

Synthesis Example 1: Synthesis of Novel Monomolecular Compound Including 1,5-naphthyridine-2,6-dione Structure (oct-NTD and oct-NTD-2Br)

Monomolecular compounds (oct-NTD and oct-NTD-2Br), which may finally be used as phosphors, were synthesized according to Synthesis Mechanism 1 below.

[Synthesis Mechanism 1]

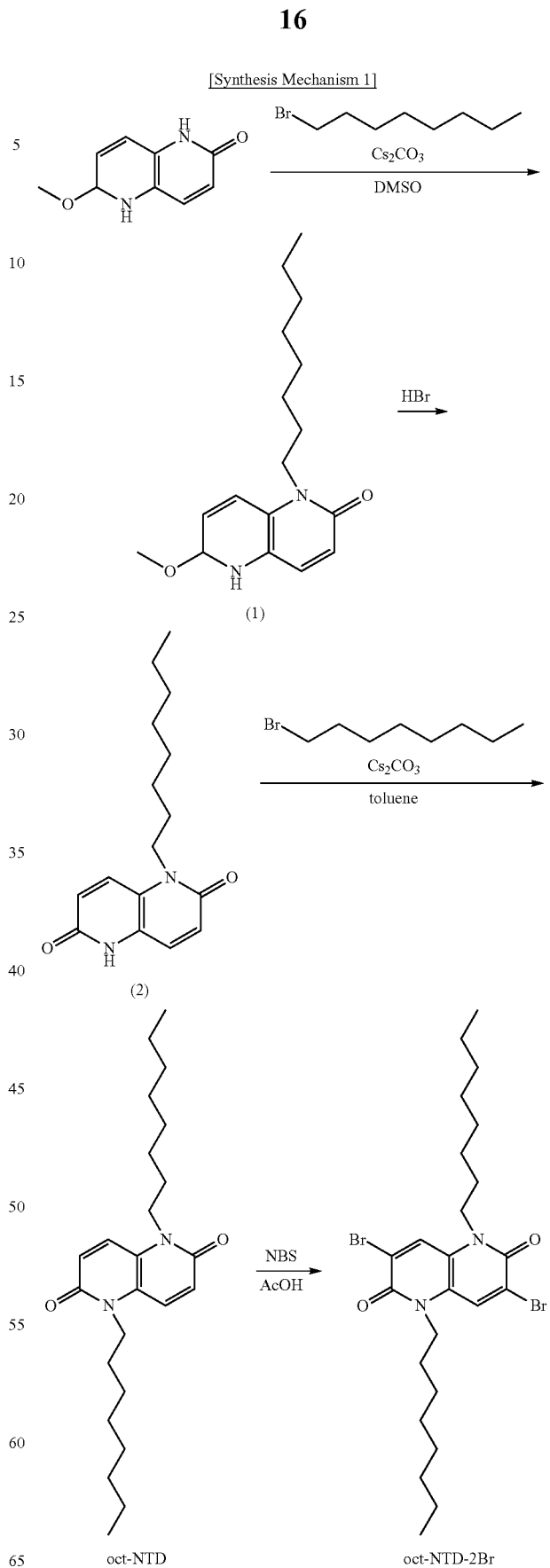

Synthesis of 6-methoxy-5-hydro-1-octyl-1,5-naphthyridin-2(1H)-one (1)

6-methoxy-1,5-naphthyridin-2(1H)-one (16 g, 90.8 mmol), cesium carbonate (32.6 g, 100 mmol), and 1-bromooctane (23.5 mL, 136 mmol) were dissolved in 160 mL of dimethyl sulfoxide (DMSO) as a solvent, and the solution was stirred at 60° C. and maintained for 24 hours. After lowering temperature to room temperature, an organic material was extracted using ethyl acetate (EA) and water and the solvent was removed in a vacuum. Then, the resultant was purified by silica gel column chromatography to obtain a yellow solid (11.1 g, yield=43%).

Synthesis of 1-octyl-5-hydro-1,5-naphthyridine-2,6-dione (2)

Material 1 (11.1 g, 38.5 mmol) was dissolved in a 48% HBr aqueous solution (80 mL), and the solution was stirred at 80° C. and maintained for 2 hours. After lowering temperature to room temperature, the pH was adjusted to 7, and then generated precipitates were washed with n-hexane for filtration and dried in a vacuum to obtain yellow powder (9.52 g, yield=90%).

Synthesis of 1,5-dioctyl-1,5-naphthyridine-2,6-dione (oct-NTD, Preparation Example 1)

Material 2 (4.5 g, 16.4 mmol), cesium carbonate (5.88 g, 18.0 mmol) and 1-bromooctane (42.5 mL, 246 mmol) were dissolved in 500 mL of toluene, and the solution was stirred at 130° C. and maintained for 24 hours. After lowering temperature to room temperature, an organic material was extracted using ethyl acetate (EA) and water, the solvent was removed in a vacuum, and the resultant was purified by silica gel column chromatography to obtain a yellow solid (2.06 g, yield=33%).

Synthesis of 3,7-dibromo-1,5-dioctyl-1,5-naphthyridine-2,6-dione (oct-NTD-2Br, Preparation Example 2)

Oct-NTD (1 g, 2.59 mmol) and N-bromosuccinimide (NBS, 1.29 g, 7.24 mmol) were dissolved in acetic acid (AA) (50 mL), and the solution was stirred at 90° C. and maintained for 24 hours. After lowering temperature to room temperature, the solvent was removed in a vacuum and the resultant was purified by silica gel column chromatography (MC:MeOH=99:1, v/v) to obtain yellow powder (0.97 g, yield=69%).

Various phosphor monomolecular compounds are synthesized by using the intermediate products of oct-NTD (Preparation Example 1) and oct-NTD-2Br (Preparation Example 2), prepared according to Synthesis Mechanism 1 above.

Synthesis of Phosphor Monomolecular Compound oct-NTDT [1,5-dioctyl-3,7-di(thiophen-2-yl)-1,5-naphthyridine-2,6-dione, Preparation Example 3]

Phosphor monomolecular compound oct-NTDT (Preparation Example 3) is synthesized using the oct-NTD-2Br (Preparation Example 2) as shown in Chemical Reaction Scheme 1 below.

[Chemical Reaction Scheme 1]

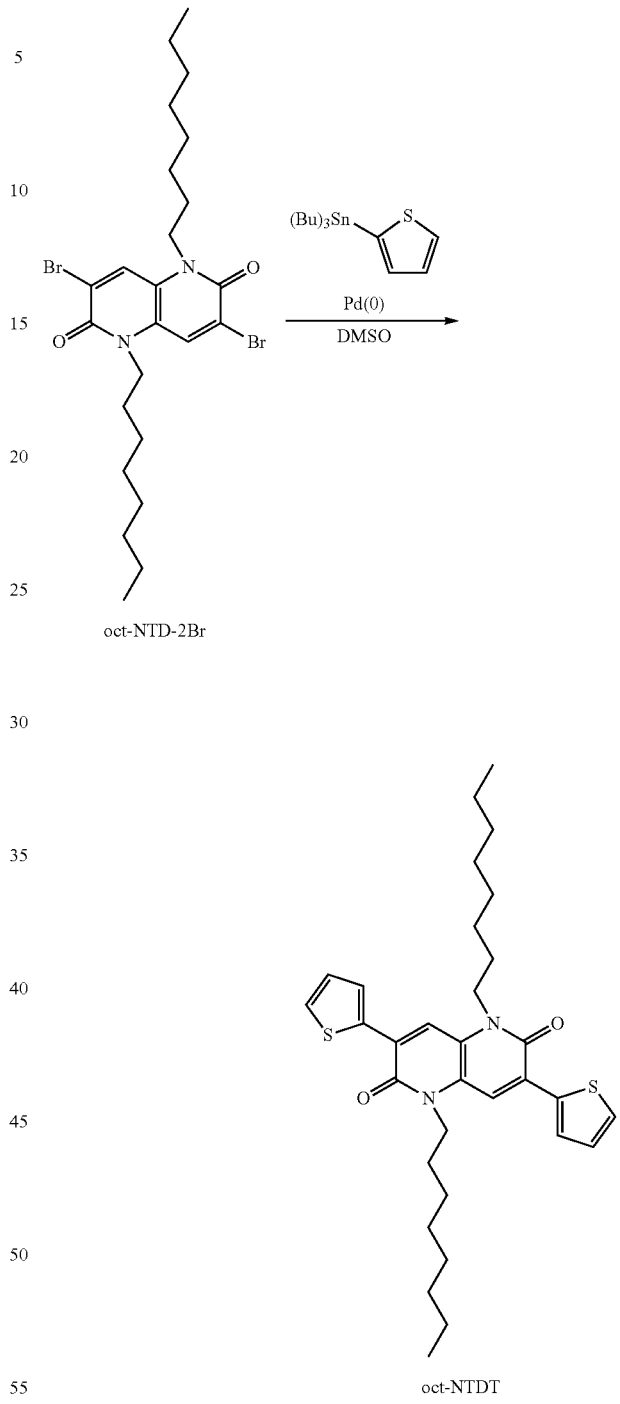

Oct-NTD-2Br (0.17 g, 0.30 mmol), 2-(tributylstannyl)thiophene (0.28 mL, 0.89 mmol), and Pd(PPh$_3$)$_4$ (0.017 g, 0.05 mmol) were dissolved in 10 mL of dimethylformamide (DMF), and the solution was stirred at 130° C. and maintained for 24 hours. After lowering temperature to room temperature, orange powder was obtained while washing with methanol (MeOH) for filtration. The resultant was purified by flash silica gel column chromatography, and recrystallized in ethyl acetate (EA) to obtain an orange solid (0.12 g, yield=74%).

Synthesis of Phosphor Monomolecular Compound oct-NTDT-2Br [3,7-bis(5-bromothiophen-2-yl)-1,5-dioctyl-1,5-naphthyridine-2,6-dione, Preparation Example 4]

Phosphor monomolecular compound oct-NTDT-2Br (Preparation Example 4) is synthesized using the oct-2NTDT (Preparation Example 3) as shown in Chemical Reaction Scheme 2 below.

[Chemical Reaction Scheme 2]

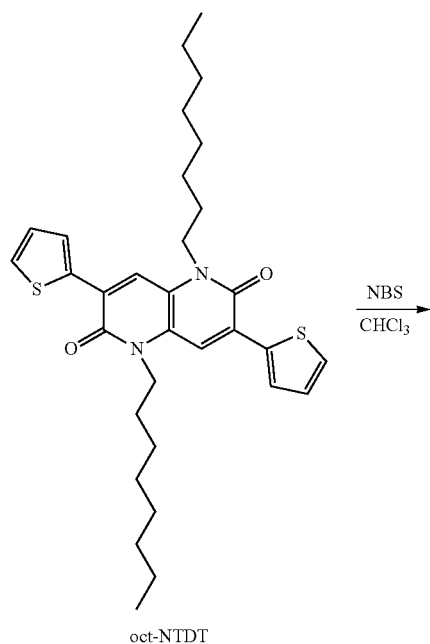

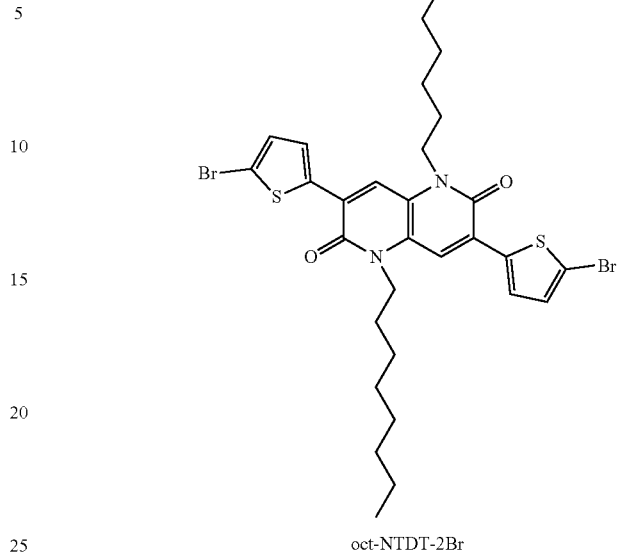

Oct-NTDT (0.25 g, 0.45 mmol) and N-bromosuccinimide (NBS, 0.19 g, 1.04 mmol) were dissolved in 25 mL chloroform ($CHCl_3$), and the solution was stirred at room temperature and maintained for 24 hours. The resultant was purified by silica gel chromatography to obtain a red solid (0.17 g, yield=53%).

Synthesis of Phosphor Monomolecular Compound oct-NTDTP-NPh₂ [3,7-bis(5-(4-(diphenylamino)phenyl)thiophen-2-yl)-1,5-dioctyl-1,5-naphthyridine-2,6-dione, Preparation Example 5]

Phosphor monomolecular compound oct-NTDTP-NPh₂ (Preparation Example 5) is synthesized using the oct-NTDT-2Br (Preparation Example 4) as shown in Chemical Reaction Scheme 3 below.

[Chemical Reaction Scheme 3]

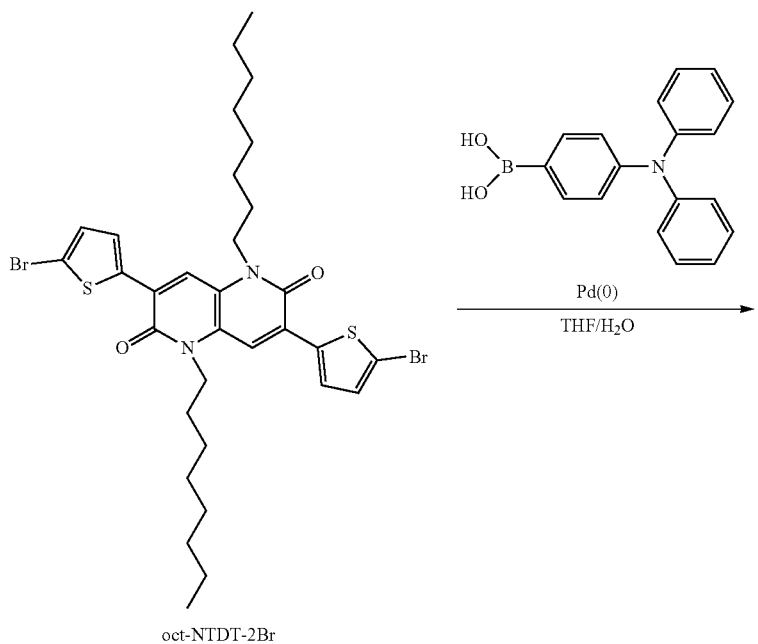

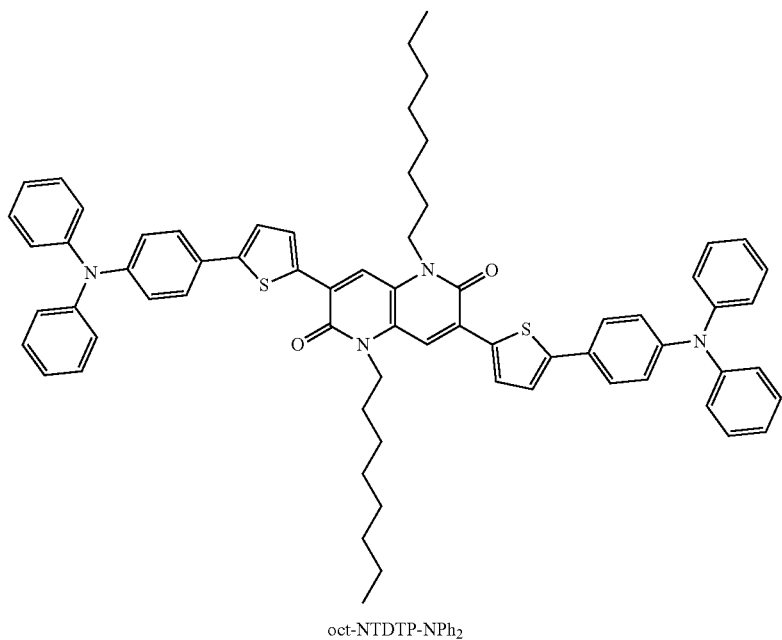

oct-NTDTP-NPh₂

Oct-NTDT-2Br (0.1 g, 0.14 mmol), 4-(diphenylamino-phenyl)boronic acid (0.12 g, 0.42 mmol), Pd(PPh₃)₄ (16 mg, 0.014 mmol), and a 1 M K₂CO₃ aqueous solution (2 mL) were added to 8 mL of tetrahydrofuran (THF), and the solution was stirred at 75° C. and maintained for 24 hours. After lowering temperature to room temperature, an organic material was extracted using ethyl acetate (EA) and water and the solvent was removed in a vacuum. The resultant was purified by silica gel column chromatography to obtain a purple solid (0.011 g, yield=8%).

Synthesis of Phosphor Monomolecular Compound oct-NTDTT [3,7-di((2,2'-bithiophe)-5-yl)-1,5-dioctyl-1,5-naphthyridine-2,6-dione, Preparation Example 6]

Phosphor monomolecular compound oct-NTDTT (Preparation Example 6) is synthesized using the oct-NTD-2Br (Preparation Example 2) as shown in Chemical Reaction Scheme 4 below.

[Chemical Reaction Scheme 4]

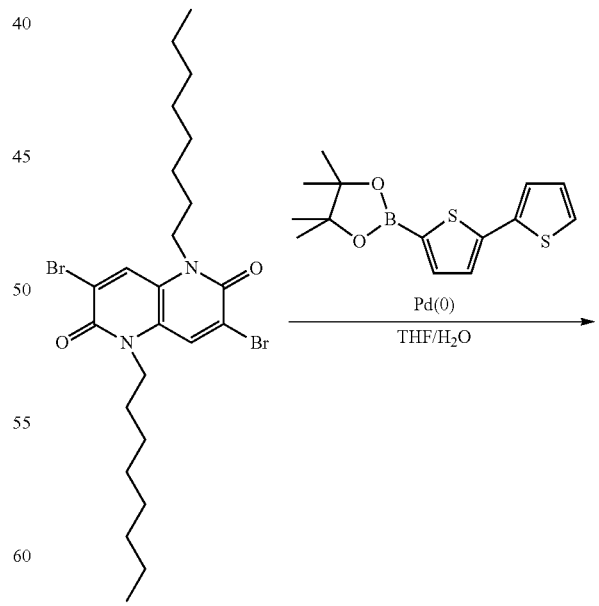

oct-NTD-2Br

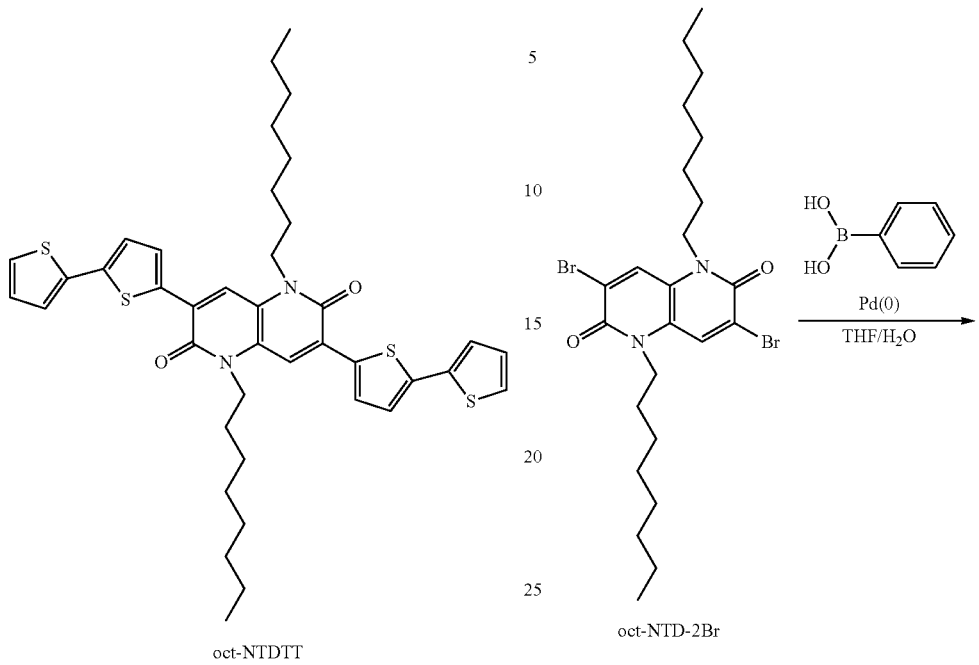

oct-NTDTT

Oct-NTD-2Br (0.1 g, 0.18 mmol), 2-[(2,2'-bithiophen)-5-yl]-4,4,5,5-tetramethyl-1,3,2-dioxaborolane (0.16 g, 0.55 mmol), Pd(PPh$_3$)$_4$ (0.021 g, 0.018 mmol), and a 1 M K$_2$CO$_3$ aqueous solution (2 mL) were added to 8 mL of tetrahydrofuran (THF), and the solution was stirred at 75° C. and maintained for 24 hours. After lowering temperature to room temperature, an organic material was extracted using ethyl acetate (EA) and water and the solvent was removed in a vacuum. The resultant was purified by silica gel chromatography to obtain a purple solid (0.077 g, yield=60%).

Synthesis of Phosphor Monomolecular Compound Oct-NTDP (1,5-dioctyl-3,7-diphenyl-1,5-naphthyridine-2,6-dione, Preparation Example 7)

Phosphor monomolecular compound oct-NTDP (Preparation Example 7) is synthesized using the oct-NTD-2Br (Preparation Example 2) as shown in Chemical Reaction Scheme 5 below.

[Chemical Reaction Scheme 5]

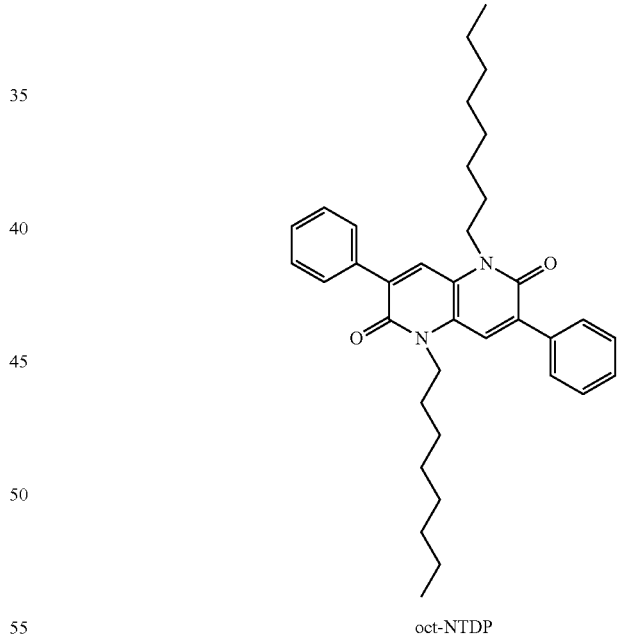

oct-NTD-2Br oct-NTDP

Oct-NTD-2Br (0.1 g, 0.18 mmol), phenylboronic acid (0.067 g, 0.55 mmol), Pd(PPh$_3$)$_4$ (0.021 g, 0.018 mmol), and a 1 M K$_2$CO$_3$ aqueous solution (2 mL) were added to 8 mL of tetrahydrofuran (THF), and the solution was stirred at 75° C. and maintained for 24 hours. After lowering temperature to room temperature, an organic material was extracted using ethyl acetate (EA) and water and the solvent was removed in a vacuum. The resultant was purified by silica gel chromatography to obtain a yellow solid (0.073 g, yield=74%).

Synthesis of Phosphor Monomolecular Compound oct-NTDP-2Br [3,7-bis(4-bromophenyl)-1,5-dioctyl-1,5-naphthyridine-2,6-dione, Preparation Example 8]

Phosphor monomolecular compound oct-NTDP-2Br (Preparation Example 8) is synthesized using the oct-NTD (Preparation Example 1) as shown in Chemical Reaction Scheme 6 below.

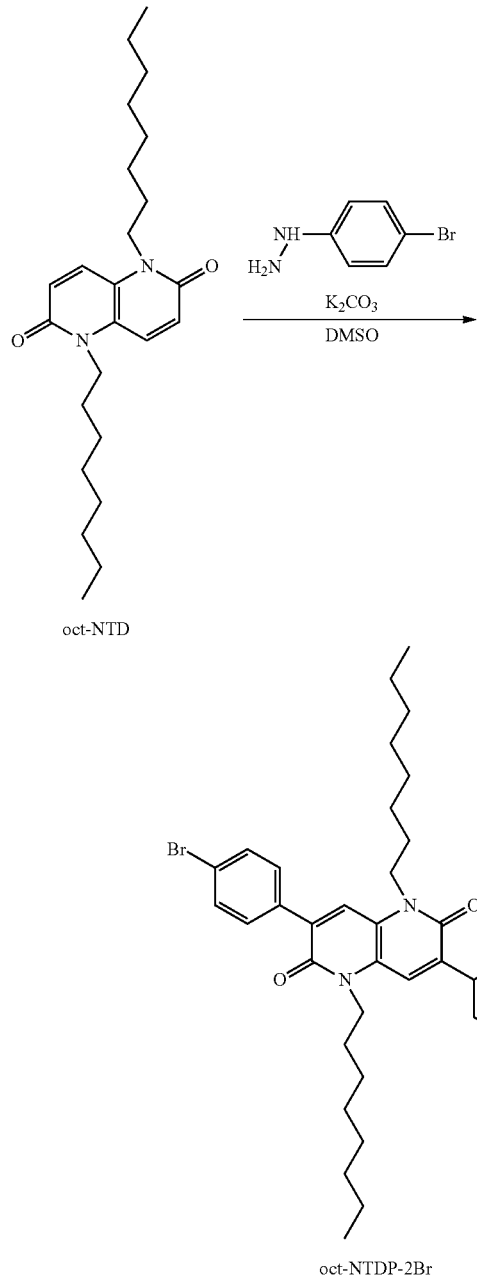

oct-NTD oct-NTDP-2Br

Oct-NTD (0.1 g, 0.26 mmol), 4-bromophenylhydrazine hydrochloride (0.14 g, 0.62 mmol), and $K_2CO_3$ (0.21 g, 1.55 mmol) were added to 15 mL of DMSO, and the solution was stirred at room temperature and maintained for 24 hours. Then, an organic material was extracted using ethyl acetate (EA) and water and the solvent was removed in a vacuum. The resultant was purified by silica gel chromatography to obtain a yellow solid. (0.022 g, yield=12%)

Synthesis of Phosphor Monomolecular Compound oct-NTDP-OMe [3,7-bis(4-methoxyphenyl)-1,5-dioctyl-1,5-naphthyridine-2,6-dione, Preparation Example 9]

Phosphor monomolecular compound oct-NTDP-OMe (Preparation Example 9) is synthesized using the oct-NTD-2Br (Preparation Example 2) as shown in Chemical Reaction Scheme 7 below.

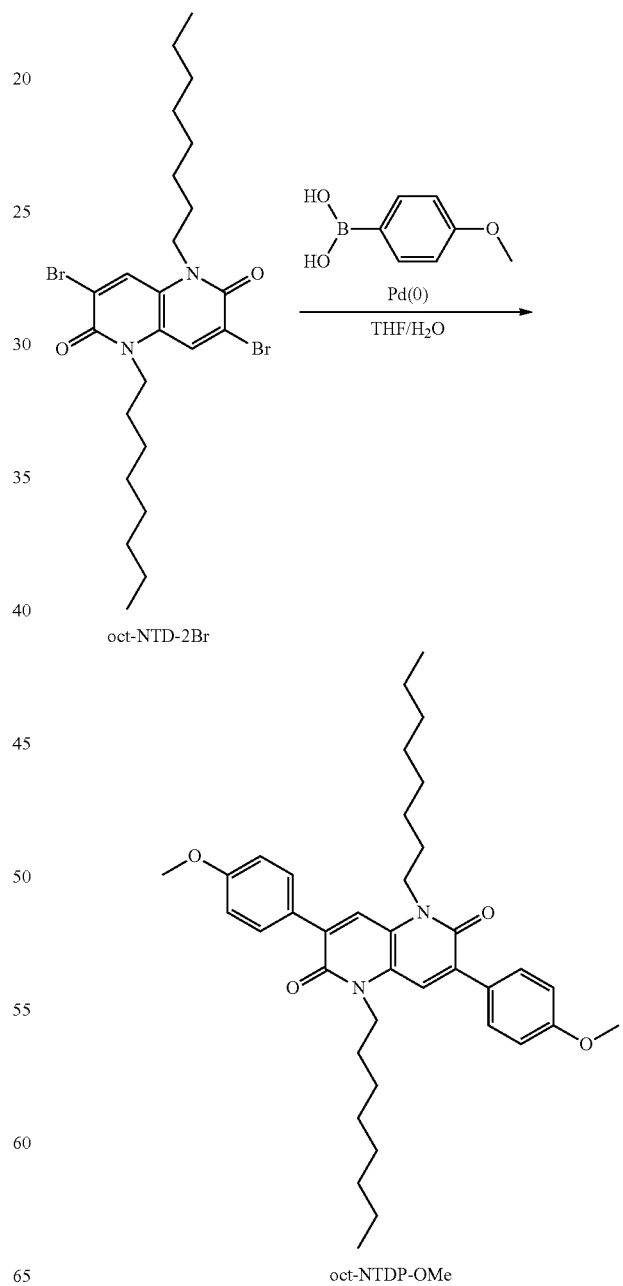

oct-NTD-2Br oct-NTDP-OMe

Oct-NTD-2Br (0.1 g, 0.18 mmol), 4-methoxyphenylboronic acid (0.084 g, 0.55 mmol), Pd(PPh$_3$)$_4$ (0.021 g, 0.018 mmol), and a 1 M K$_2$CO$_3$ aqueous solution (2 mL) were added to 8 mL of tetrahydrofuran (THF), and the solution was stirred at 75° C. and maintained for 24 hours. After lowering temperature to room temperature, an organic material was extracted using ethyl acetate (EA) and water and the solvent was removed in a vacuum. The resultant was purified by silica gel chromatography to obtain a yellow solid (0.90 g, yield=83%).

Synthesis of Phosphor Monomolecular Compound oct-NTDP-NMe$_2$ [3,7-bis(4-(dimethylamino)phenyl)-1,5-dioctyl-1,5-naphthyridine-2,6-dione, Preparation Example 10]

Phosphor monomolecular compound oct-NTDP-NMe$_2$ (Preparation Example 10) is synthesized using the oct-NTD-2Br (Preparation Example 2) as shown in Chemical Reaction Scheme 8 below.

[Chemical Reaction Scheme 8]

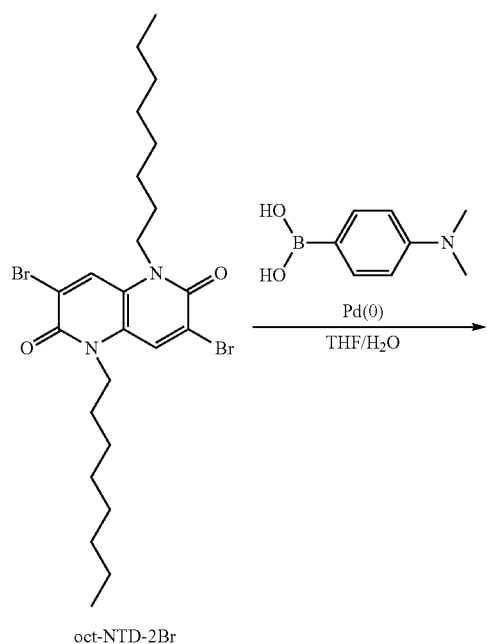

oct-NTD-2Br

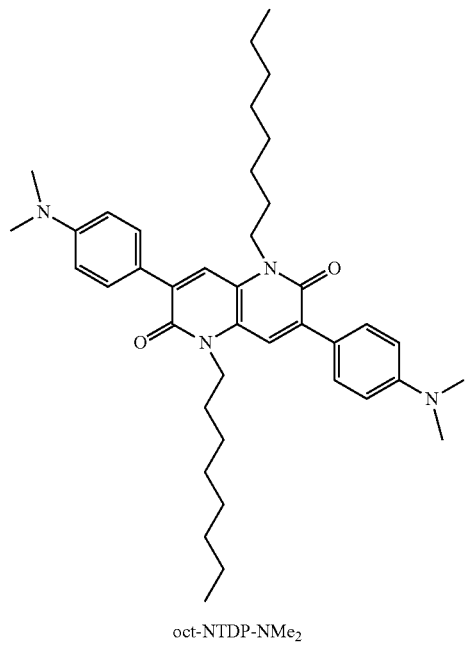

oct-NTDP-NMe$_2$

Oct-NTD-2Br (0.1 g, 0.18 mmol), 4-(dimethylaminophenyl)boronic acid (0.091 g, 0.55 mmol), Pd(PPh$_3$)$_4$ (0.021 g, 0.018 mmol), and a 1 M K$_2$CO$_3$ aqueous solution (2 mL) were added to 8 mL of tetrahydrofuran (THF), and the solution was stirred at 75° C. and maintained for 24 hours. After lowering temperature to room temperature, an organic material was extracted using ethyl acetate (EA) and water and the solvent was removed in a vacuum. The resultant was purified by silica gel chromatography to obtain a yellow solid (0.086 g, yield=76%).

Synthesis of Phosphor Monomolecular Compound oct-NTDP-NPh$_2$ [3,7-bis(4-(diphenylamino)phenyl)-1,5-dioctyl-1,5-naphthyridine-2,6-dione, Preparation Example 11]

Phosphor monomolecular compound oct-NTDP-NPh$_2$ (Preparation Example 11) is synthesized using the oct-NTD-2Br (Preparation Example 2) as shown in Chemical Reaction Scheme 9 below.

[Chemical Reaction Scheme 9]

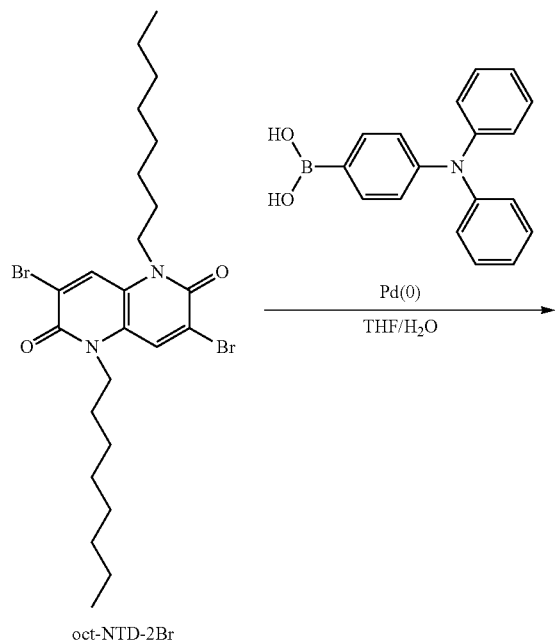

oct-NTD-2Br → oct-NTDP-NPh2

Oct-NTD-2Br (0.1 g, 0.18 mmol), 4-(diphenylaminophenyl)boronic acid (0.16 g, 0.55 mmol), Pd(PPh$_3$)$_4$ (0.021 g, 0.018 mmol), and a 1 M K$_2$CO$_3$ aqueous solution (2 mL) were added to 8 mL of tetrahydrofuran (THF), and the solution was stirred at 75° C. and maintained for 24 hours. After lowering temperature to room temperature, an organic material was extracted using ethyl acetate (EA) and water and the solvent was removed in a vacuum. The resultant was purified by silica gel chromatography to obtain a yellow solid (0.12 g, yield=76%).

Synthesis of Phosphor Monomolecular Compound oct-NTDN1 [3,7-di(naphthalen-1-yl)-1,5-dioctyl-1,5-naphthyridine-2,6-dione, Preparation Example 12]

Phosphor monomolecular compound oct-NTDN1 (Preparation Example 12) is synthesized using the oct-NTD-2Br (Preparation Example 2) as shown in Chemical Reaction Scheme 10 below.

[Chemical Reaction Scheme 10]

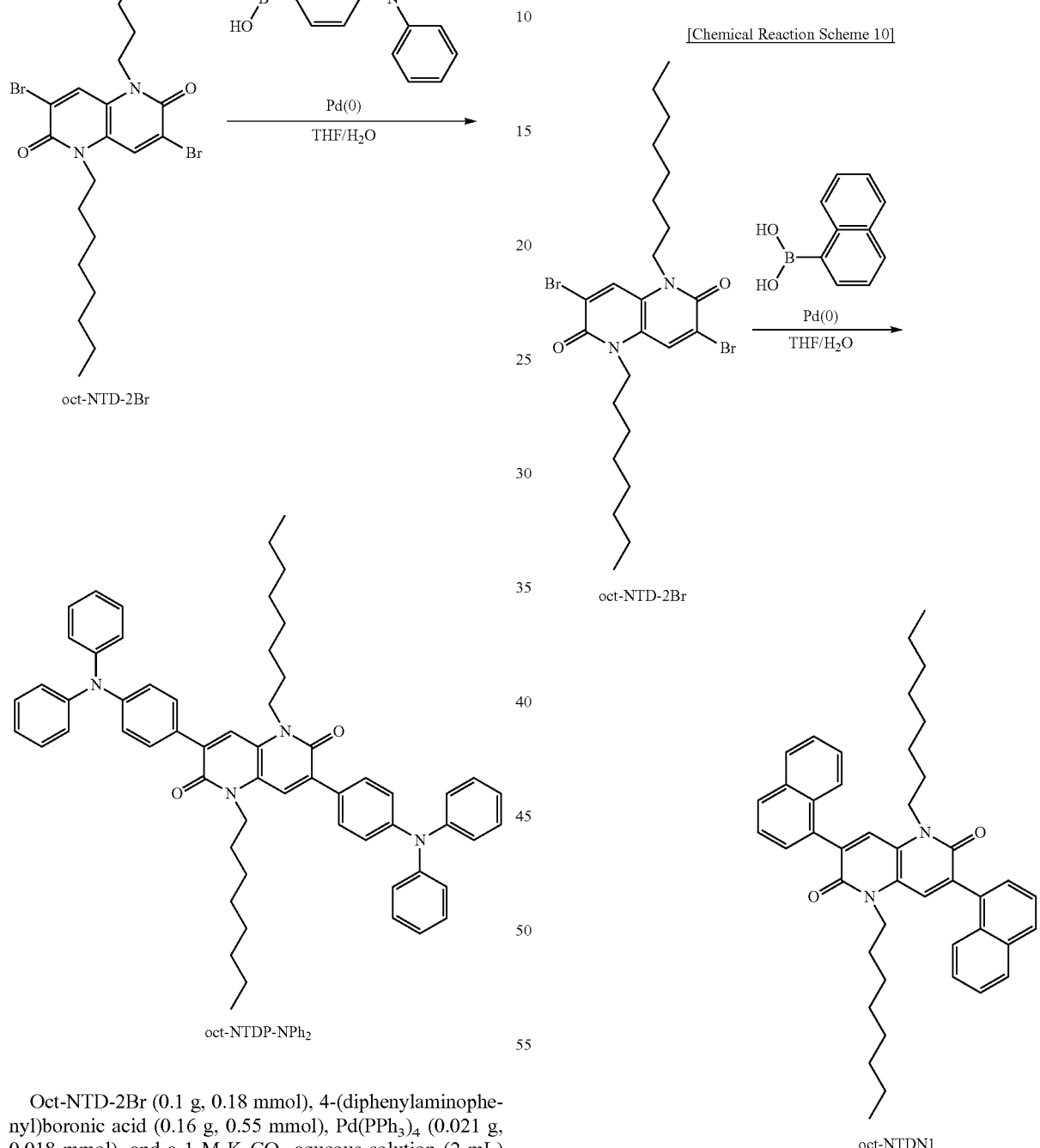

oct-NTD-2Br → oct-NTDN1

Oct-NTD-2Br (0.2 g, 0.37 mmol), naphthalen-1-yl-boronic acid (0.19 g, 1.10 mmol), Pd(PPh$_3$)$_4$ (0.042 g, 0.037 mmol), and a 1 M K$_2$CO$_3$ aqueous solution (6 mL) were added to 24 mL of tetrahydrofuran (THF), and the solution was stirred at 75° C. and maintained for 24 hours. After lowering temperature to room temperature, an organic material was extracted using ethyl acetate (EA) and water and the solvent was removed in a vacuum. The resultant was purified by silica gel chromatography to obtain a yellow solid (0.14 g, yield=58%).

Synthesis of Phosphor Monomolecular Compound oct-NTDN2 [3,7-di(naphthalen-2-yl)-1,5-dioctyl-1,5-naphthyridine-2,6-dione, Preparation Example 13]

Phosphor monomolecular compound oct-NTDN2 (Preparation Example 13) is synthesized using the oct-NTD-2Br (Preparation Example 2) as shown in Chemical Reaction Scheme 11 below.

Oct-NTD-2Br (0.2 g, 0.37 mmol), naphthalen-2-yl-boronic acid (0.19 g, 1.10 mmol), Pd(PPh$_3$)$_4$ (0.042 g, 0.037 mmol), and a 1 M K$_2$CO$_3$ aqueous solution (6 mL) were added to 24 mL of tetrahydrofuran (THF), and the solution was stirred at 75° C. and maintained for 24 hours. After lowering temperature to room temperature, an organic material was extracted using ethyl acetate (EA) and water and the solvent was removed in a vacuum. The resultant was purified by silica gel chromatography to obtain a yellow solid (0.18 g, yield=78%).

Synthesis of Phosphor Monomolecular Compound oct-NTDPy [3,7-di(pyridin-4-yl)-1,5-dioctyl-1,5-naphthyridine-2,6-dione, Preparation Example 14]

Phosphor monomolecular compound oct-NTDPy (Preparation Example 14) is synthesized using the oct-NTD-2Br (Preparation Example 2) as shown in Chemical Reaction Scheme 12 below.

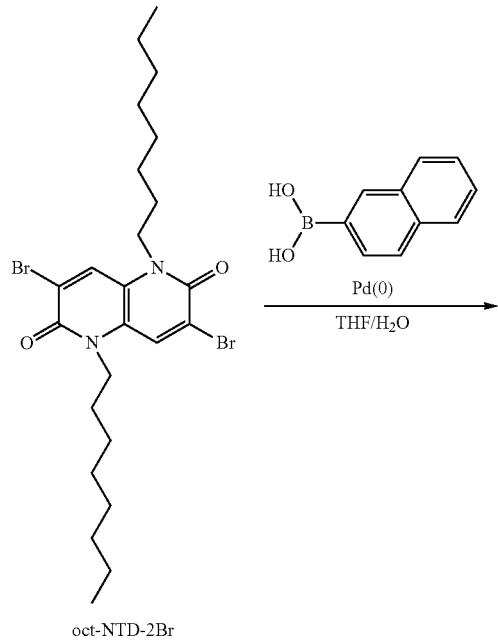

[Chemical Reaction Scheme 11]

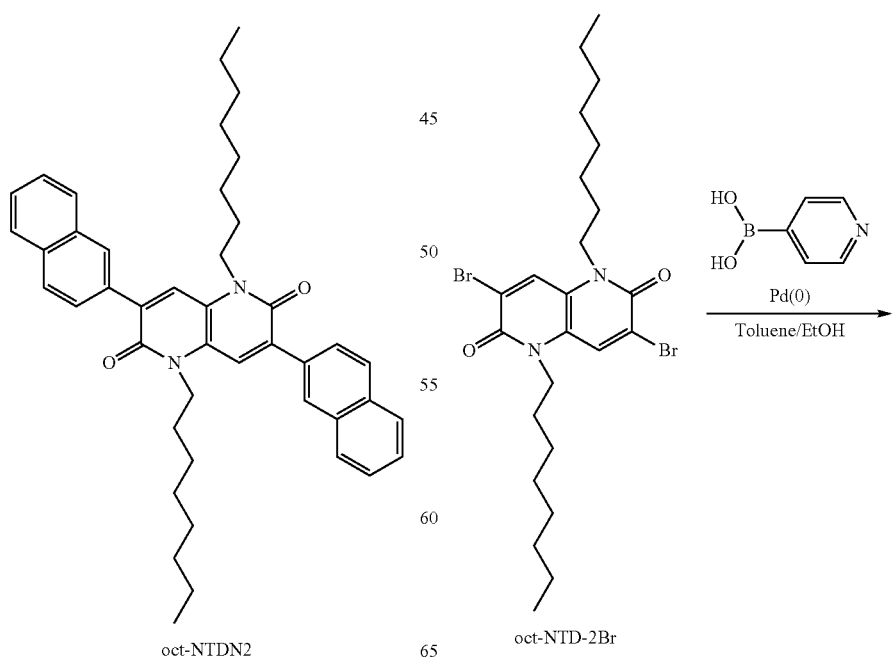

[Chemical Reaction Scheme 12]

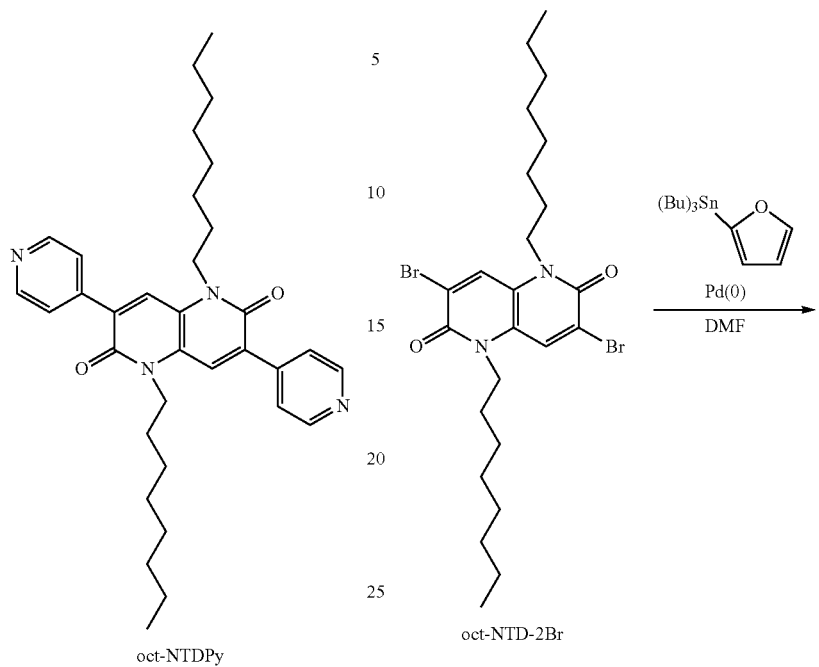

oct-NTDPy

Oct-NTD-2Br (0.2 g, 0.37 mmol), pyridin-4-yl-boronic acid (0.135 g, 1.10 mmol), Pd(PPh$_3$)$_4$ (0.042 g, 0.037 mmol), and 1.11 g of K$_2$CO$_3$ were added to 8 mL of ethanol and 24 mL of toluene, and the solution was stirred at 70° C. and maintained for 24 hours. After lowering temperature to room temperature, an organic material was extracted using ethyl acetate (EA) and water and the solvent was removed in a vacuum. The resultant was purified by silica gel chromatography to obtain an orange solid (0.15 g, yield=76%).

Synthesis of Phosphor Monomolecular Compound oct-NTDF [3,7-di(furan-2-yl)-1,5-dioctyl-1,5-naphthyridine-2,6-dione, Preparation Example 15]

Phosphor monomolecular compound oct-NTDF (Preparation Example 15) is synthesized using the oct-NTD-2Br (Preparation Example 2) as shown in Chemical Reaction Scheme 13 below.

[Chemical Reaction Scheme 13]

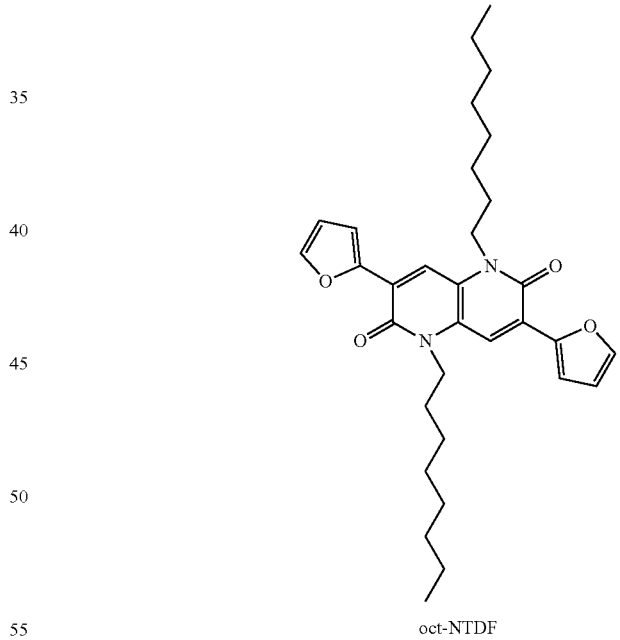

oct-NTD-2Br oct-NTDF

Oct-NTD-2Br (0.2 g, 0.37 mmol), 2-tributylstannyl)furan (0.39 g, 1.10 mmol), and Pd(PPh$_3$)$_4$ (0.042 g, 0.037 mmol) were added to 5 mL of DMF, and the solution was stirred at 130° C. and maintained for 24 hours. After lowering temperature to room temperature, an organic material was extracted using ethyl acetate (EA) and water and the solvent was removed in a vacuum. The resultant was purified by silica gel chromatography to obtain an orange solid (0.14 g, yield=73%).

Synthesis Example 2: Synthesis of Novel Monomolecular Compound Including 1,5-naphthyridine-2,6-dione Structure (TEG-NTD and TEG-NTD-2Br)

Monomolecular compounds (oct-NTD and oct-NTD-2Br), which may finally be used as phosphors, were synthesized according to Synthesis Mechanism 2 below.

[Synthesis Mechanism 2]

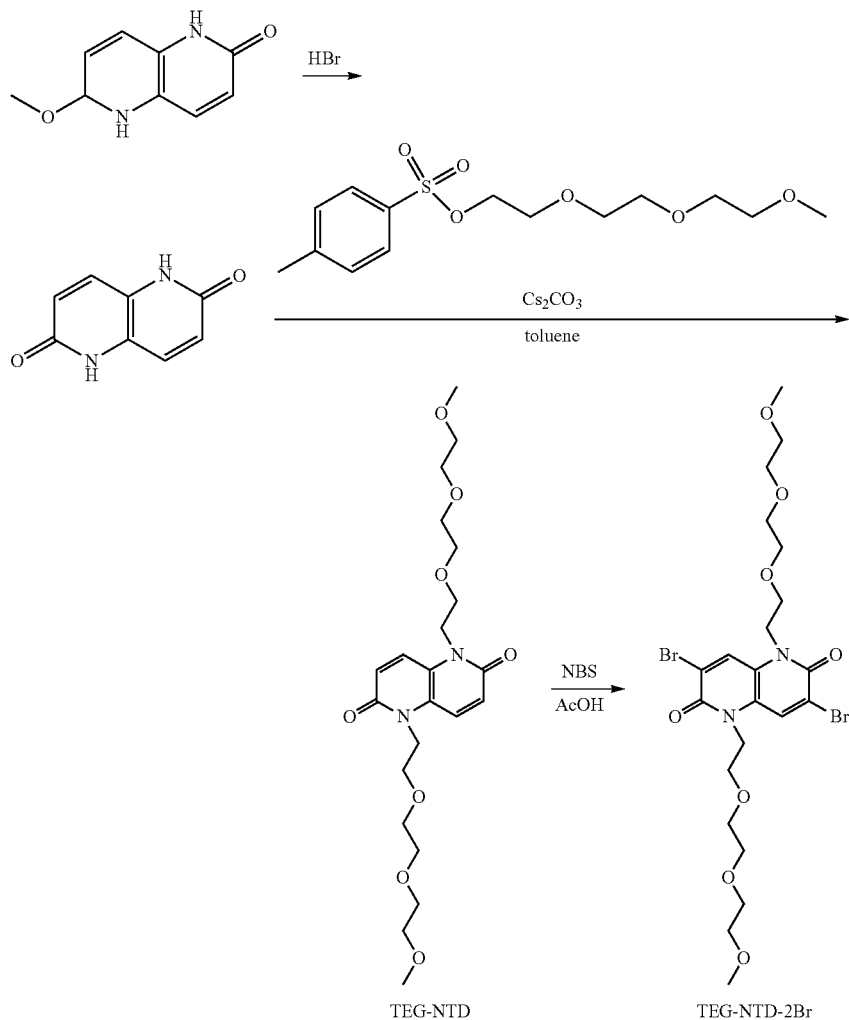

TEG-NTD         TEG-NTD-2Br

Detailed Synthesis Method

Synthesis of 1,5-hydro-1,5-naphthyridine-2,6-dione (3)

6-methoxy-1,5-naphthyridin-2(1H)-one (5 g, 28.4 mmol) was dissolved in 100 mL of a 48% HBr aqueous solution, and the solution was stirred at 80° C. and maintained for 2 hours. After lowering temperature to room temperature, the pH was adjusted to 7, and then generated precipitates were washed with n-hexane for filtration and dried in a vacuum to obtain a beige solid (4.43 g, yield=96%).

Synthesis of 1,5-bis(2-(2-(2-methoxyethoxy)ethoxy)ethyl)-1,5-naphthyridine-2,6-dione (TEG-NTD, Preparation Example 16)

Material (3) (1 g, 6.17 mmol), 2-(2-(2-methoxyethoxy)ethoxy)ethyl-4-methylbenzenesulfonate (9.82 g, 30.8 mmol), and cesium carbonate (4.42 g, 13.6 mmol) were dissolved in 500 mL of toluene, and the solution was stirred at 130° C. and maintained for 24 hours. After lowering temperature to room temperature, an organic material was extracted using ethyl acetate (EA) and water, the solvent was removed in a vacuum, and purified by silica gel column chromatography to obtain a yellow solid (0.19 g, yield=7%).

Synthesis of 3,7-dibromo-1,5-bis(2-(2-(2-methoxyethoxy)ethoxy)ethyl)-1,5-naphthyridine-2,6-dione (TEG-NTD-2Br, Preparation Example 17)

TEG-NTD (0.14 g, 0.31 mmol) and N-bromosuccinimide (NBS, 0.15 g, 0.86 mmol) were dissolved in 10 mL of acetic acid (AA), and the solution was stirred at 90° C. and maintained for 24 hours. After lowering temperature to room temperature, the solvent was removed in a vacuum, and purified by silica gel column chromatography (MC:MeOH=99:1, v/v) to obtain yellow powder (0.055 g, yield=29%).

Synthesis of Phosphor Monomolecular Compound TEG-NTDT [1,5-bis(2-(2-(2-methoxyethoxy)ethoxy)ethyl)-3,7-di(thiophen-2-yl)-1,5-naphthyridine-2,6-dione, Preparation Example 18]

Phosphor monomolecular compound TEG-NTDT (Preparation Example 18) is synthesized using the TEG-NTD-2Br (Preparation Example 17) as shown in Chemical Reaction Scheme 14 below.

[Chemical Reaction Scheme 14]

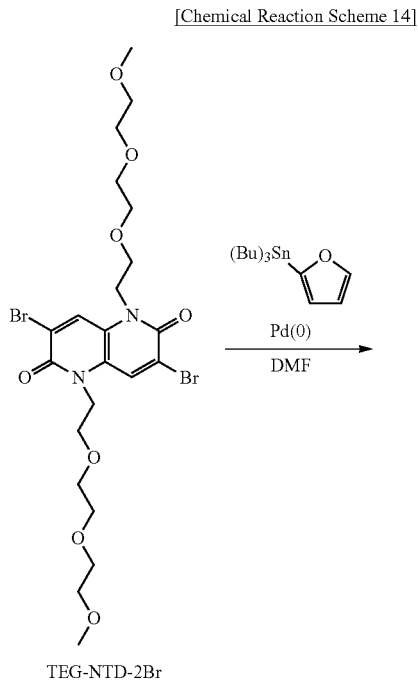

TEG-NTD-2Br

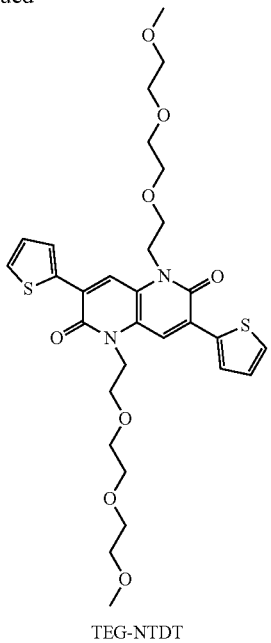

TEG-NTDT

TEG-NTD-2Br (0.050 g, 0.082 mmol), 2-(tributylstannyl)thiophene (0.078 mL, 0.25 mmol), and Pd(PPh$_3$)$_4$ (0.094 g, 0.0082 mmol) were dissolved in 10 mL of dimethylformamide (DMF), and the solution was stirred at 130° C. and maintained for 24 hours. After lowering temperature to room temperature, an organic material was extracted using ethyl acetate (EA) and water and the solvent was removed in a vacuum. The resultant was purified by silica gel chromatography to obtain an orange solid (0.028 g, yield=55%).

Table 1 below shows various monomolecular compounds prepared according to the synthesis methods as described above.

TABLE 1

| Preparation Example 1 |
|---|
| 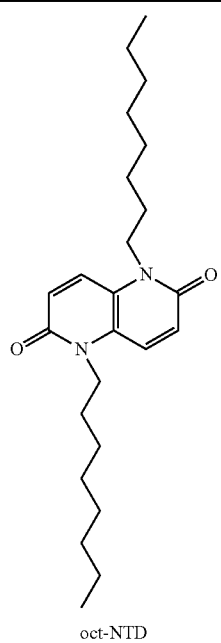 |
| oct-NTD |

TABLE 1-continued
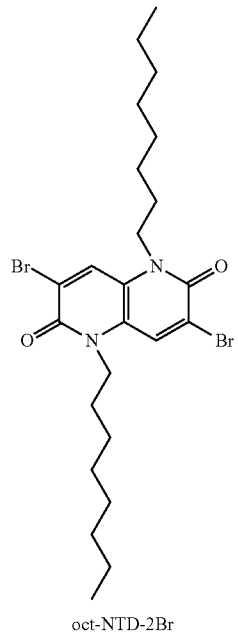 [SMILES: CCCCCCCCn1c(=O)c(Br)cc2c1cc(Br)c(=O)n2CCCCCCCC]
oct-NTD-2Br
Preparation Example 2
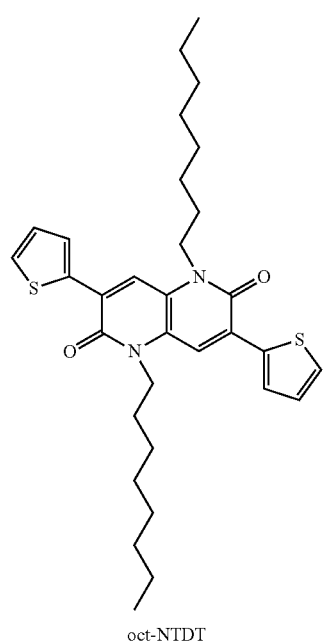 [SMILES: CCCCCCCCn1c(=O)c(-c2cccs2)cc2c1cc(-c1cccs1)c(=O)n2CCCCCCCC]
oct-NTDT
Preparation Example 3

TABLE 1-continued
Preparation Example 4
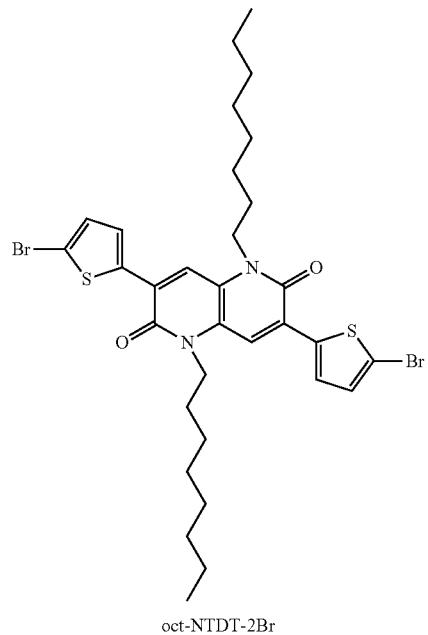 [SMILES: CCCCCCCCn1c(=O)c(-c2ccc(Br)s2)cc2c1cc(-c1ccc(Br)s1)c(=O)n2CCCCCCCC]
oct-NTDT-2Br
Preparation Example 5
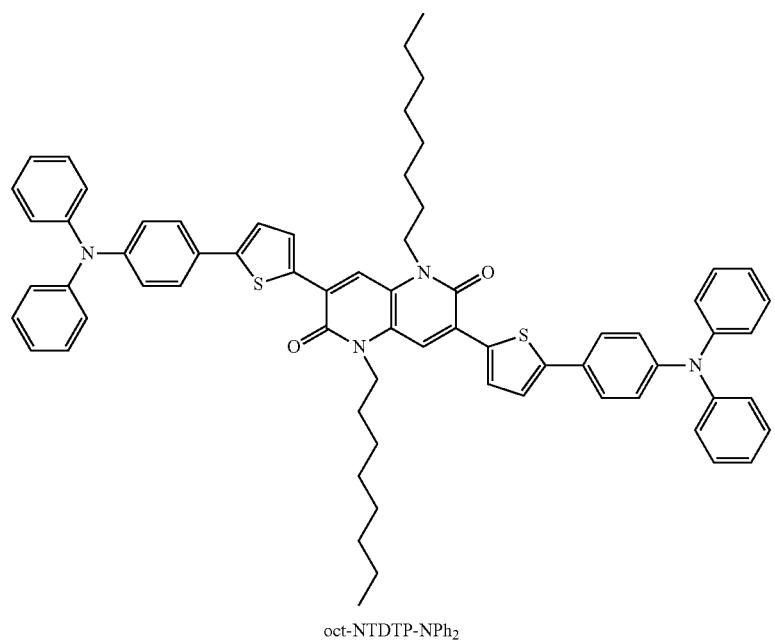 [SMILES: CCCCCCCCn1c(=O)c(-c2ccc(-c3ccc(N(c4ccccc4)c4ccccc4)cc3)s2)cc2c1cc(-c1ccc(-c3ccc(N(c4ccccc4)c4ccccc4)cc3)s1)c(=O)n2CCCCCCCC]
oct-NTDTP-NPh$_2$ TABLE 1-continued
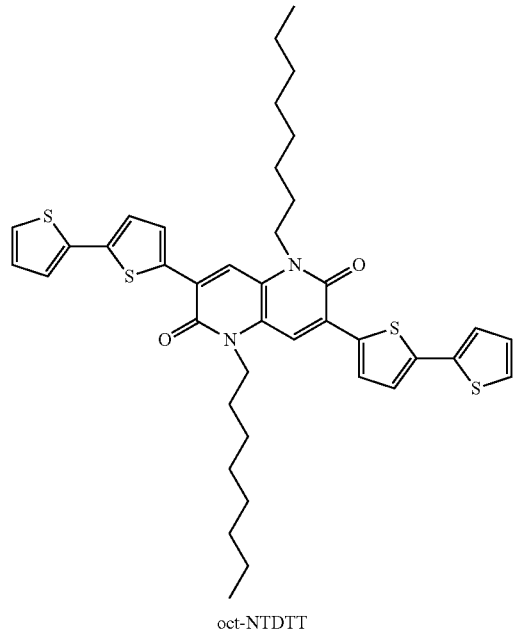 [SMILES: CCCCCCCCn1c(=O)c(-c2ccc(-c3cccs3)s2)cc2c1cc(-c1ccc(-c3cccs3)s1)c(=O)n2CCCCCCCC]
oct-NTDTT
Preparation Example 6
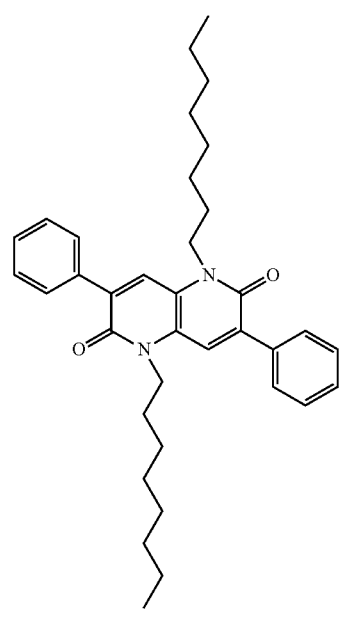
oct-NTDP
Preparation Example 7

TABLE 1-continued
Preparation Example 8
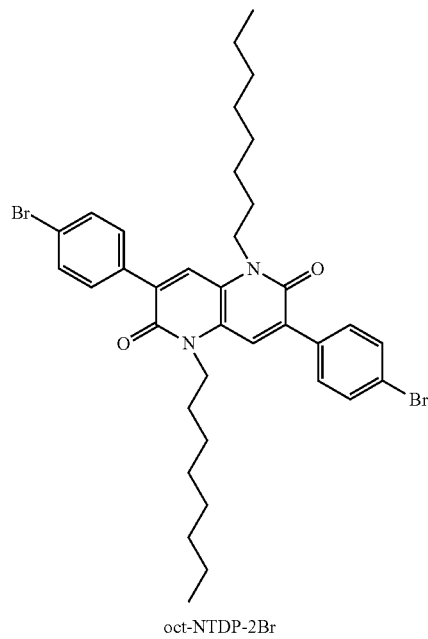 [SMILES: CCCCCCCCn1c(=O)c(-c2ccc(Br)cc2)cc2c1cc(-c1ccc(Br)cc1)c(=O)n2CCCCCCCC]
oct-NTDP-2Br
Preparation Example 9
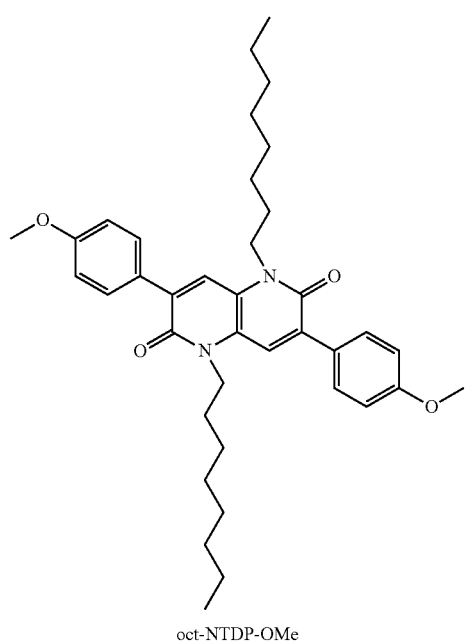
oct-NTDP-OMe TABLE 1-continued
Preparation Example 10
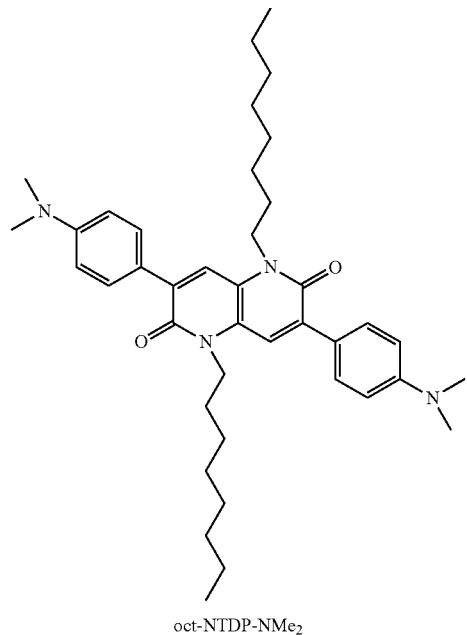
oct-NTDP-NMe₂
Preparation Example 11
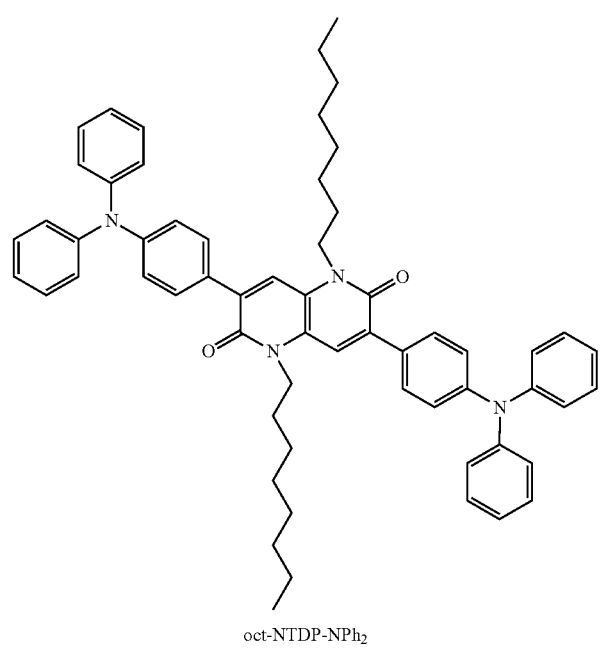 [SMILES: CCCCCCCCn1c(=O)c(-c2ccc(N(c3ccccc3)c3ccccc3)cc2)cc2c1cc(-c1ccc(N(c3ccccc3)c3ccccc3)cc1)c(=O)n2CCCCCCCC]
oct-NTDP-NPh₂

TABLE 1-continued
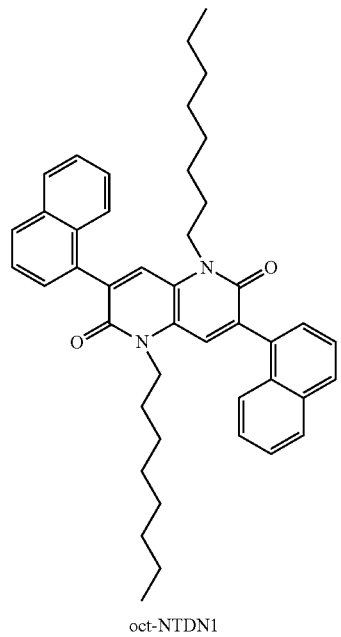 [SMILES: CCCCCCCCn1c(=O)c(-c2cccc3ccccc23)cc2c1cc(-c1cccc3ccccc13)c(=O)n2CCCCCCCC]
oct-NTDN1
Preparation Example 12
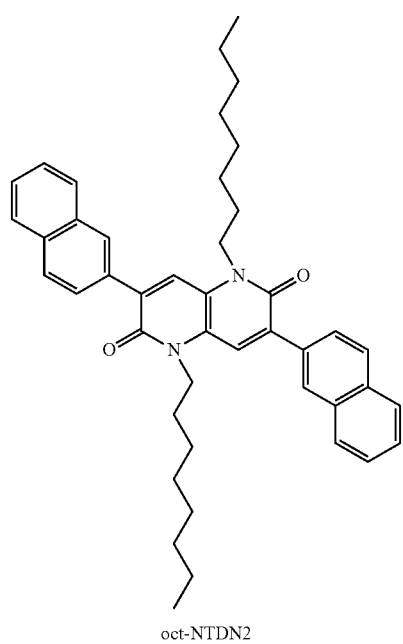 [SMILES: CCCCCCCCn1c(=O)c(-c2ccc3ccccc3c2)cc2c1cc(-c1ccc3ccccc3c1)c(=O)n2CCCCCCCC]
oct-NTDN2
Preparation Example 13

TABLE 1-continued
Preparation Example 14
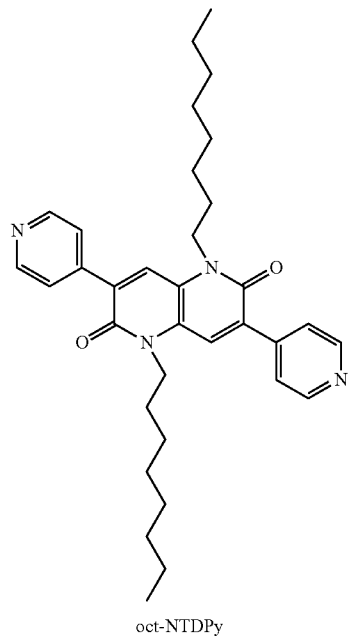 [SMILES: CCCCCCCCn1c(=O)c(-c2ccncc2)cc2c1cc(-c1ccncc1)c(=O)n2CCCCCCCC]
oct-NTDPy
Preparation Example 15
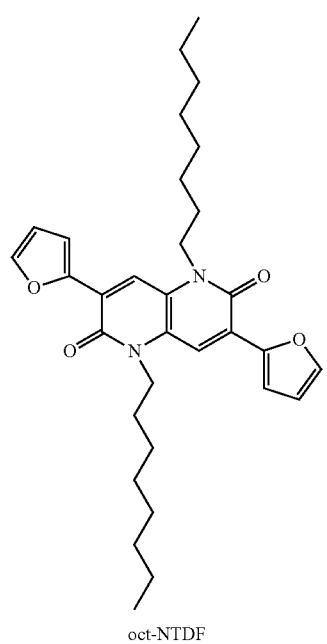 [SMILES: CCCCCCCCn1c(=O)c(-c2ccco2)cc2c1cc(-c1ccco1)c(=O)n2CCCCCCCC]
oct-NTDF TABLE 1-continued
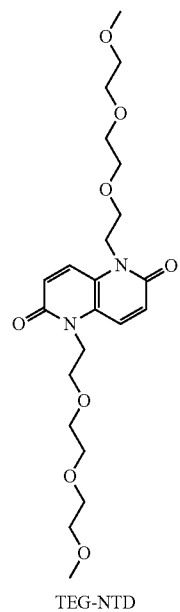 [SMILES: COCCOCCOCCn1c(=O)ccc2c1ccc(=O)n2CCOCCOCCOC]
TEG-NTD
Preparation Example 16
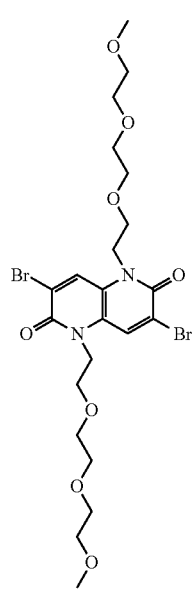
TEG-NTD-2Br
Preparation Example 17

TABLE 1-continued

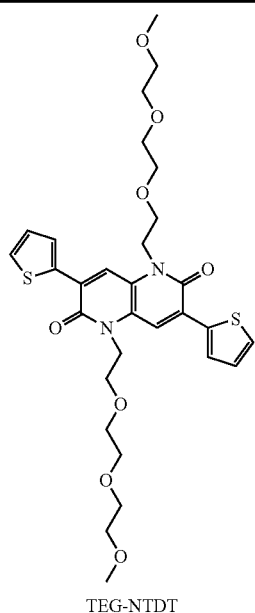

Preparation Example 18

TEG-NTDT

Hereinafter, experiments on photoluminescence characteristics of the prepared phosphor monomolecular compounds and performance evaluation as organic transistor devices and water oxidation photocatalyst will be described.

Figure 3A:
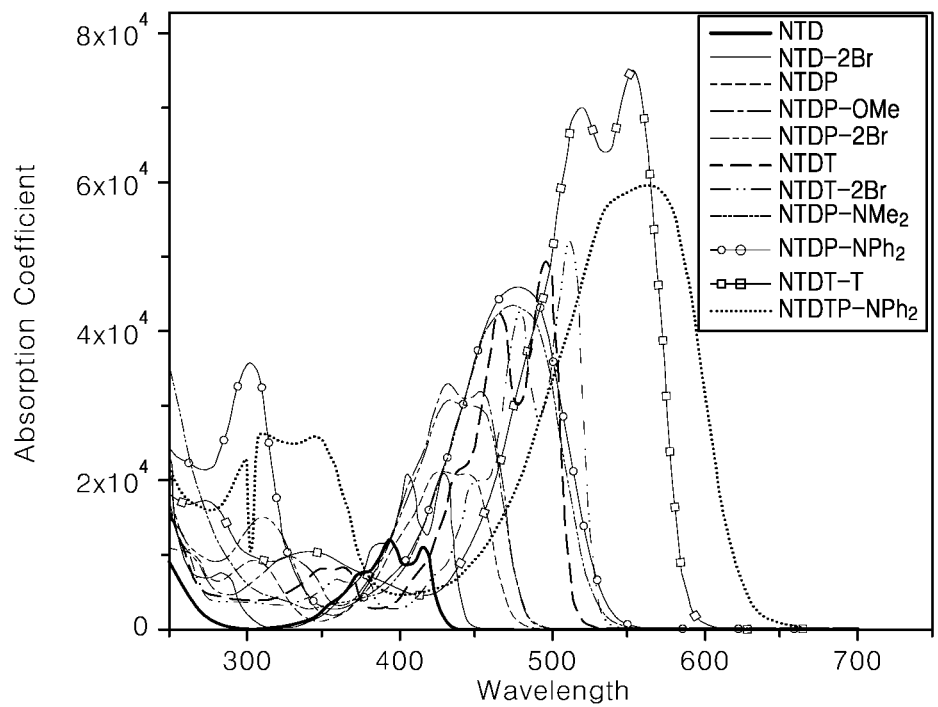
FIGS. 3A, 3B and 3C show graphs illustrating light absorption spectra of phosphor monomolecular compounds according to an embodiment of the present invention.
Figure 3B:
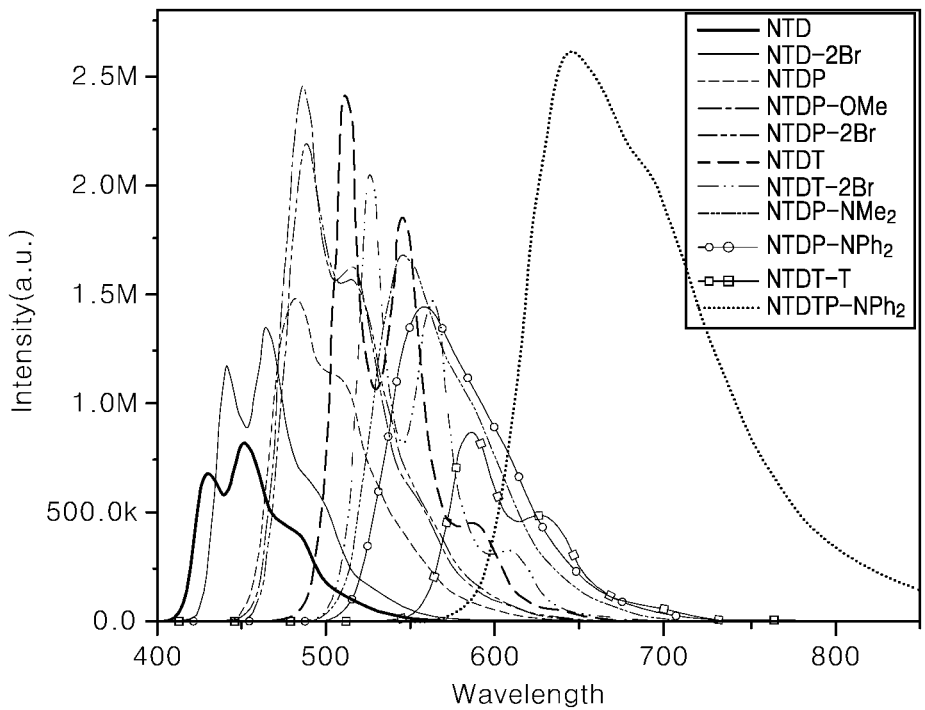
Figure 3C:
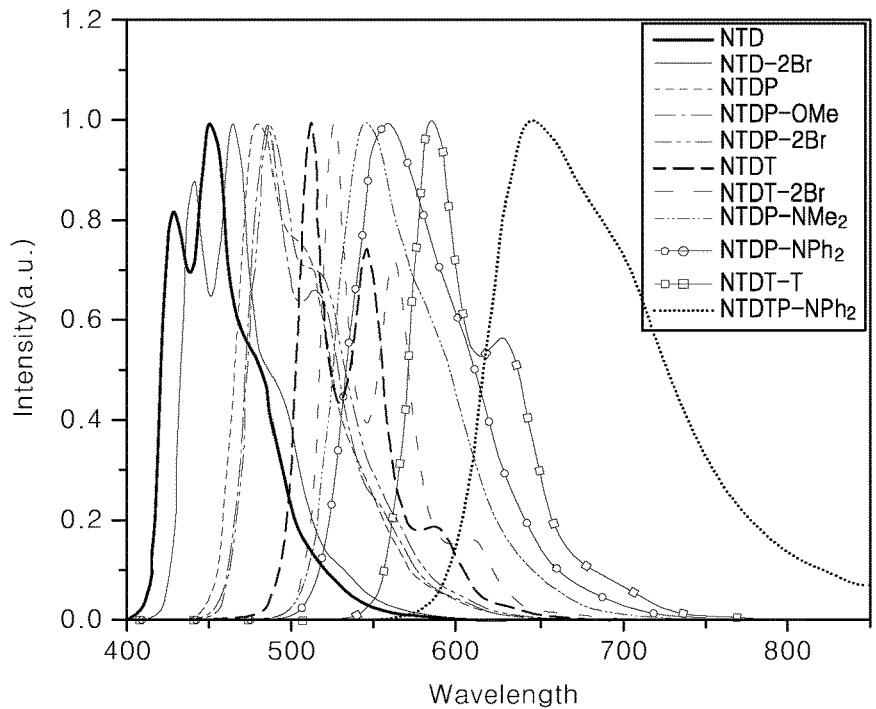
Figure 4A:
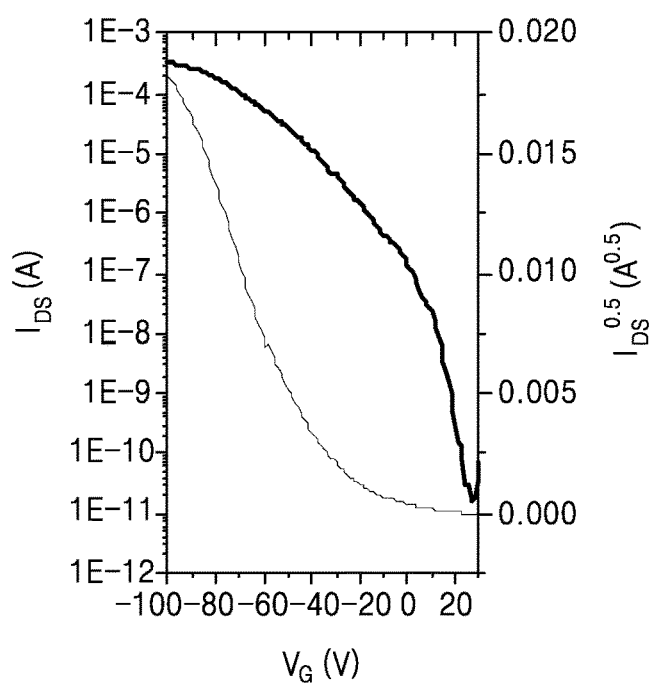
FIGS. 4A, 4B, 4C, 4D, 4E and 4F show graphs illustrating transfer curves of organic transistors according to an embodiment of the present invention.
Figure 4B:
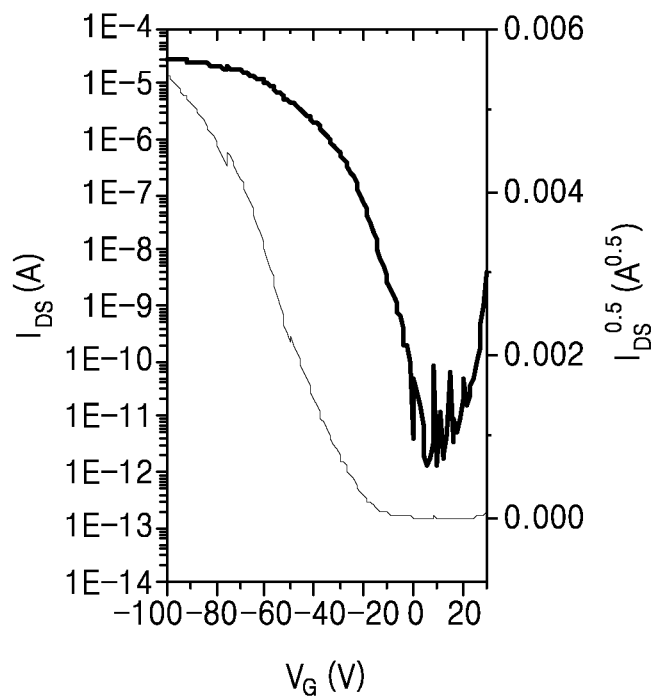
Figure 4C:
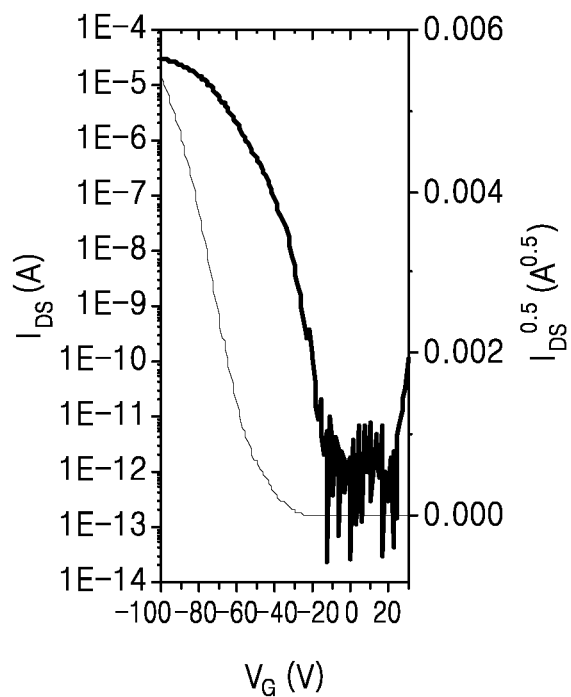
Figure 4D:
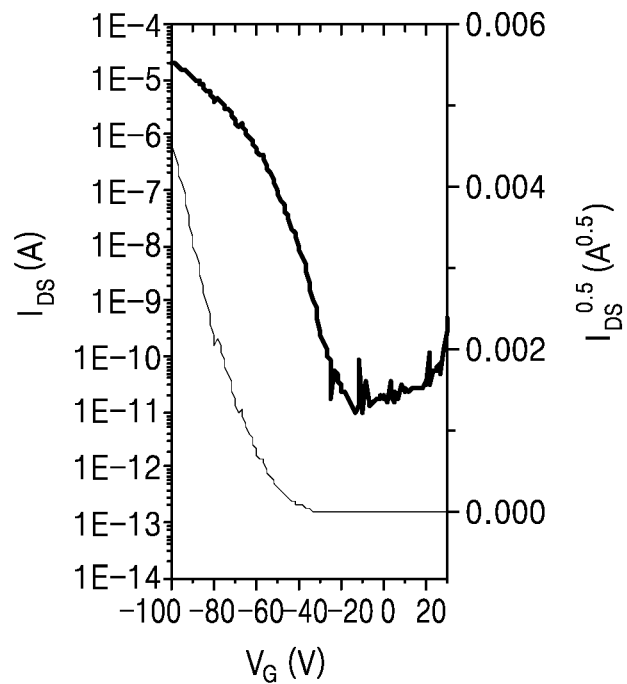
Figure 4E:
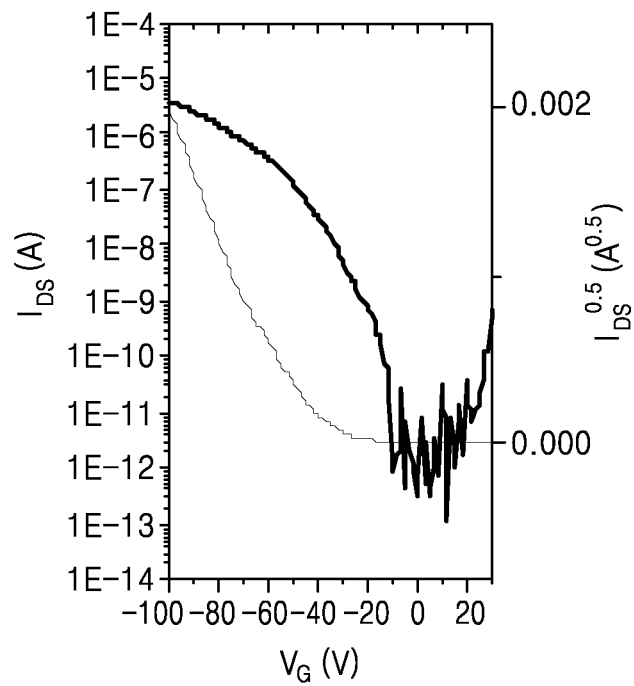
Figure 4F:
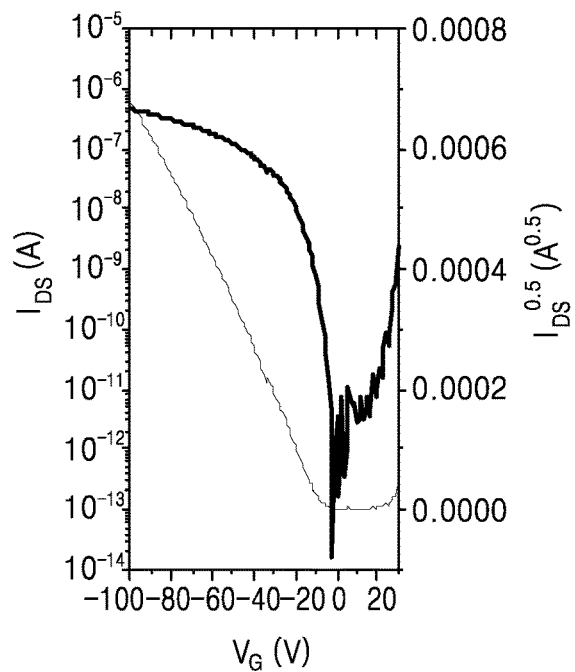

Experimental Example 1: Experiment on Photoluminescence Characteristics of Phosphor Monomolecular Compounds Photoluminescence characteristics of the monomolecular compounds synthesized according to Preparation Examples 1 to 18 as phosphor monomolecular compounds were examined. Stoke solutions of the compounds of Preparation Examples 1 to 15 were prepared using $10^{-3}$ M chloroform ($CHCl_3$), and $CHCl_3$ solution samples diluted to $10^{-5}$ M were prepared. Each of the prepared samples was added to a cuvette and absorption spectrum thereof was obtained by UV/Vis spectroscopy. The measured absorption spectrum results are shown in FIGS. 3A to 3C.

In addition, photoluminescence quantum yields (PLQY) of the compounds obtained according to Preparation Examples 1 to 18 were measured by photoluminescence spectroscopy. The measured results are shown in Table 2 below. In the cases of Preparation Examples 16 to 18, quantum yields were measured in aqueous solutions and $CHCl_3$ phases, respectively.

TABLE 2

| | Photoluminescence quantum yield ($\phi_{relative}$) |
|---|---|
| Preparation Example 1 | 0.88 |
| Preparation Example 2 | 0.95 |
| Preparation Example 3 | 1 |
| Preparation Example 4 | 0.94 |
| Preparation Example 5 | 1 |
| Preparation Example 6 | 0.42 |
| Preparation Example 7 | 1 |
| Preparation Example 8 | 1 |
| Preparation Example 9 | 1 |
| Preparation Example 10 | 0.82 |

TABLE 2-continued

| Preparation Example 11 | 1 |
|---|---|
| Preparation Example 12 | 0.25 |
| Preparation Example 13 | 0.64 |
| Preparation Example 14 | 1 |
| Preparation Example 15 | 0.65 |

| | Photoluminescence quantum yield ($\phi_{absolute}$), In $H_2O$ | Photoluminescence quantum yield ($\phi_{absolute}$), In $CHCl_3$ |
|---|---|---|
| Preparation Example 16 | 1 | 0.98 |
| Preparation Example 17 | 0.97 | 0.95 |
| Preparation Example 18 | 1 | 0.98 |

FIGS. 3A to 3C show graphs illustrating light absorption spectra of phosphor monomolecular compounds according to an embodiment of the present invention. FIG. 3A shows absorption spectra according to the preparation examples, FIG. 3B shows emission spectra, and FIG. 3C shows average spectra.

Referring to FIGS. 3A to 3C, it may be confirmed that the phosphor monomolecular compounds according to the preparation examples of the present invention exhibit excellent absorption spectra in a wide range of wavelengths.

In addition, as shown in Table 2 above, high photoluminescence quantum yields may be obtained.

Experimental Example 2: Evaluation Experiment on Performance of Organic Transistor Device Evaluation experiments on performance of p-type organic transistor devices respectively manufactured by forming semiconductor layers using the phosphor monomolecular compounds according to Preparation Examples 3, 6, 7, 12, 13, and 15.

A silicon substrate ($SiO_2$/Si) was washed with acetone and isopropanol by sonication and treated with UV-ozone for 20 minutes. In addition, after the surface of a silicon layer ($SiO_2$) of the substrate was treated with a gas-phase octadecyltrichlorosilane (OTS), the substrate was transferred to a glove box and the compound according to Preparation Example 3 was thermally deposited thereon in a high vacuum pressure ($10^{-6}$ to $10^{-5}$ torr). Then, gold (Au) was thermally deposited thereon in a high vacuum pressure to form a source electrode and a drain electrode, thereby manufacturing a p-type organic field-effect transistor (OFET) device having a top contact-bottom gate structure. A hole mobility was measured in a saturation region of the manufactured transistor device, and the results are shown in FIGS. 4A to 5C and Table 3 below.

TABLE 3

| Material | Temperature ($T_{sub}$) | Average Hole Mobility ($\mu_{p, avg}$) | Maximum Hole Mobility ($\mu_{p, max}$) |
|---|---|---|---|
| Preparation Example 3 (oct-NTDT) | 110° C. | 1.08 cm$^2$/Vs | 2.76 cm$^2$/Vs |
| Preparation Example 6 (oct-NTDTT) | 70° C. | 0.086 cm$^2$/Vs | 0.17 cm$^2$/Vs |
| Preparation Example 7 (oct-NTDP) | 25° C. | 0.12 cm$^2$/Vs | 0.34 cm$^2$/Vs |
| Preparation Example 12 (oct-NTDN1) | 70° C. | 0.12 cm$^2$/Vs | 0.30 cm$^2$/Vs |
| Preparation Example 13 (oct-NTDN2) | 70° C. | 0.022 cm$^2$/Vs | 0.036 cm$^2$/Vs |
| Preparation Example 15 (oct-NTDF) | 25° C. | 0.0097 cm$^2$/Vs | 0.018 cm$^2$/Vs |

Figure 5A:
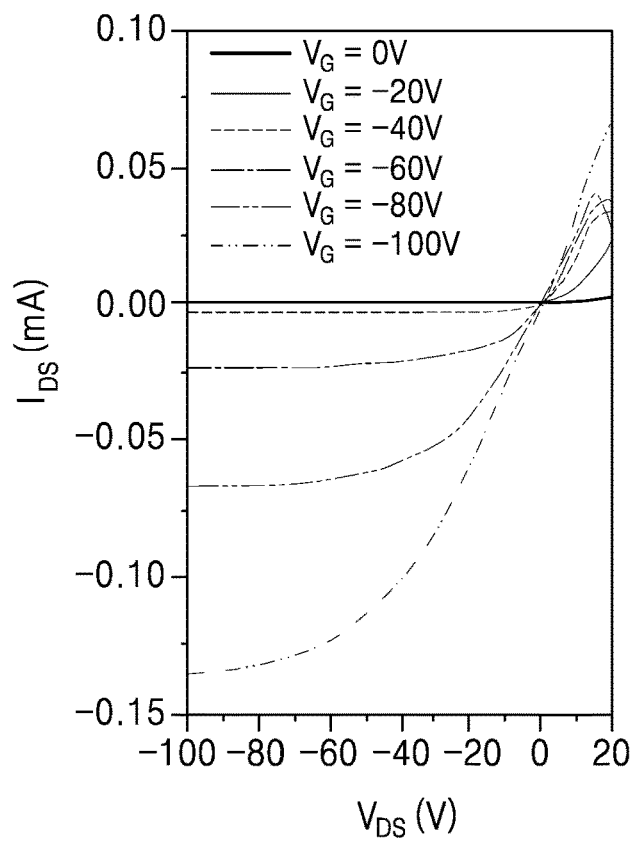
FIGS. 5A, 5B and 5C show graphs illustrating output curves of organic transistors according to an embodiment of the present invention.
Figure 5B:
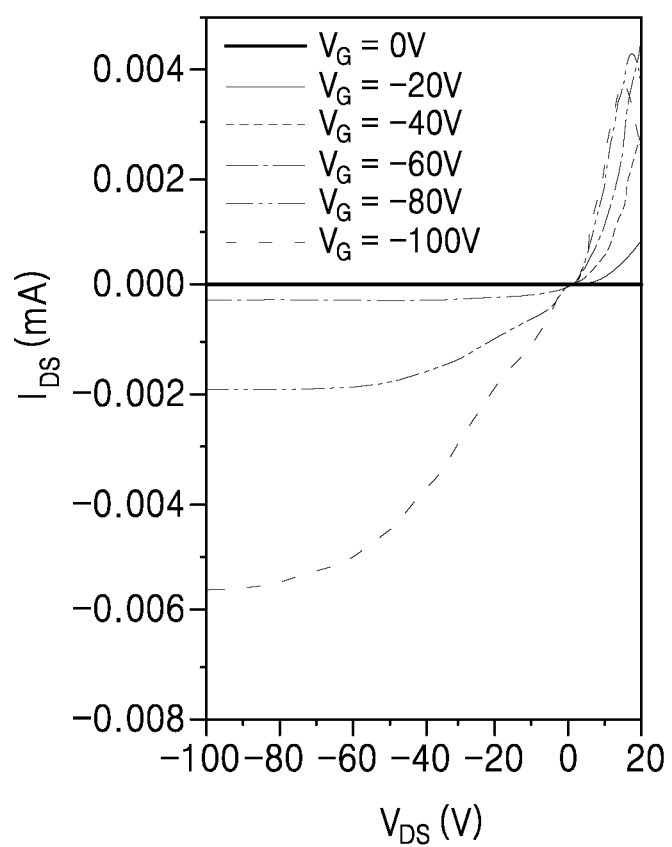
Figure 5C:
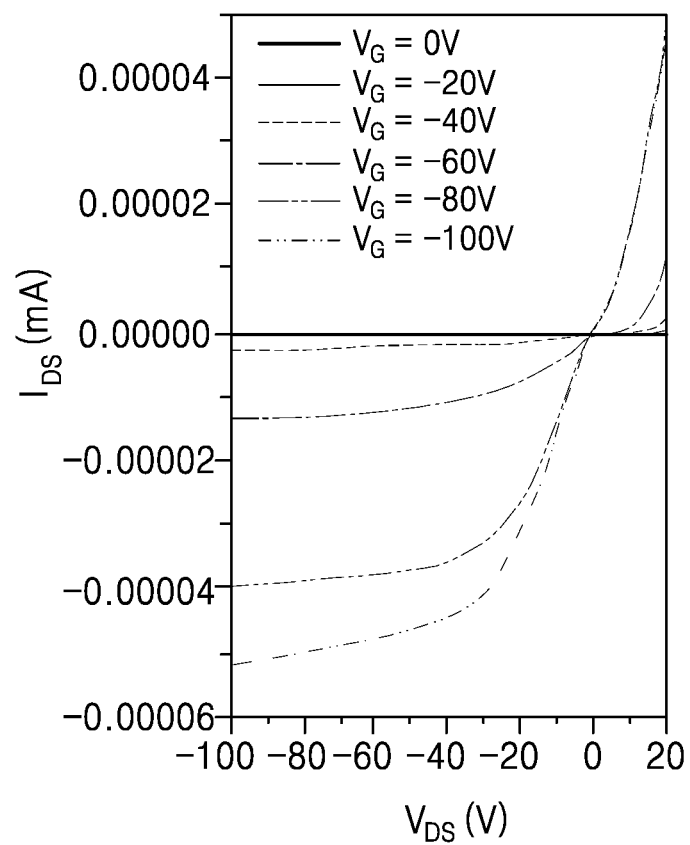

FIGS. 4A to 5C show graphs illustrating results of performance evaluation on organic transistors according to an embodiment of the present invention. FIGS. 4A to 4F show transfer curves of organic transistors manufactured using the phosphor monomolecular compounds according to Preparation Examples 3, 6, 7, 12, 13, and 15, respectively, and FIGS. 5A to 5C show output curves of organic transistors manufactured using the phosphor monomolecular compounds according to Preparation Examples 3, 7, and 15, respectively.

Referring to FIGS. 4A to 5C, it may be confirmed that the organic transistors according to the preparation examples have high on-off ratios. It may also be confirmed that the curves are relatively linear with respect to gate voltage (Vg) and currents may flow in the organic transistors by a small voltage. That is, it may be confirmed that the organic transistors including the phosphor monomolecular compounds according to the present invention have excellent performance.

Experimental Example 3: Evaluation Experiment on Activity of Water Splitting and Hydrogen Production Catalyst Evaluation experiments on activity of the photocatalyst were conducted by using the phosphor monomolecular compound prepared according to Preparation Example 3 as a water splitting and hydrogen production catalyst for hydrogen production.

2 mg of the compound according to Preparation Example 3 was dissolved in a co-solvent of water/THF (6:4, v/v) in a vial for hydrogen production, and 0.5 mL of triethylamine, as an electron donor, was added thereto. After replacing the inside of the vial with argon (Ar) gas, a 400 nm long pass filter was mounted on a 300 W Xenon lamp to emit light from which UV region has been removed. In this regard, the amount of hydrogen generated in the vial was measured every hour. In addition, an amount of generated hydrogen was measured under the same conditions except that g-CN powder was added instead of the compound of Preparation Example 3 and the results are shown in FIG. 6.

Figure 6:
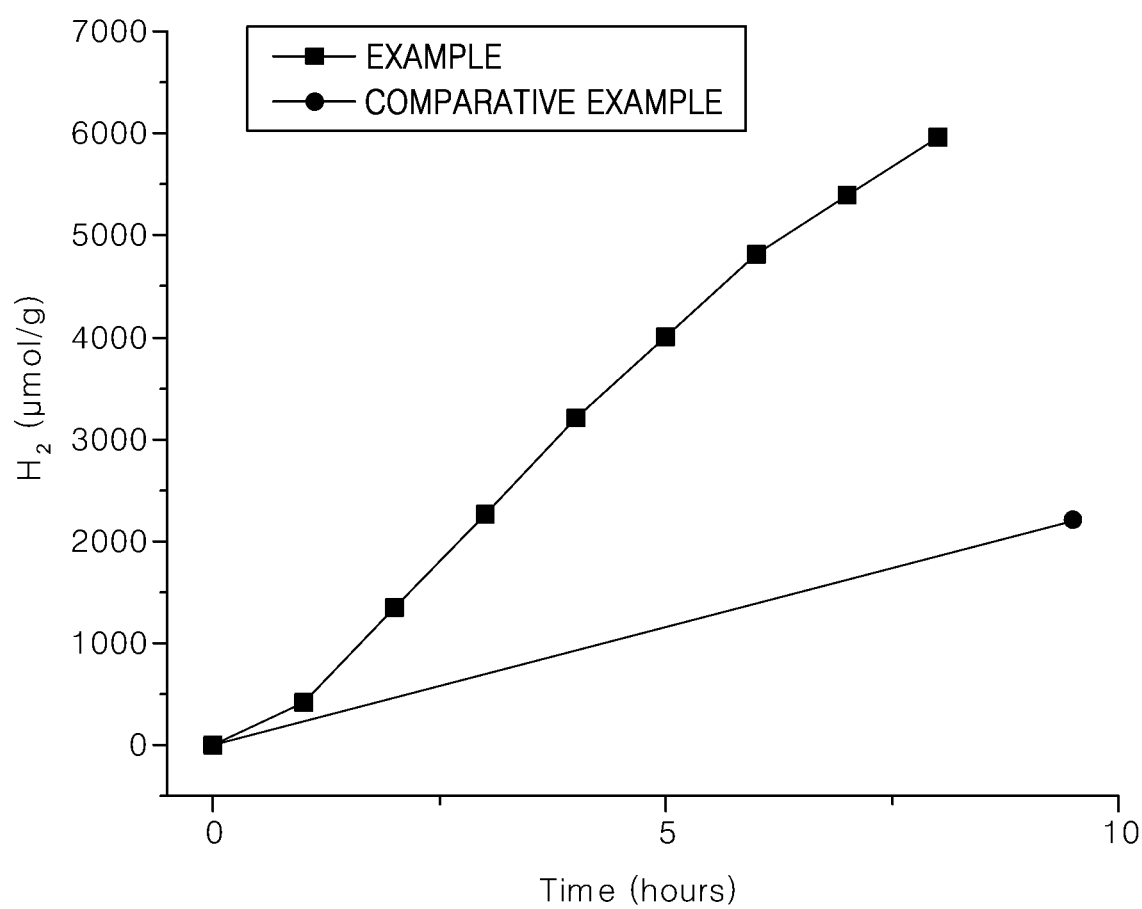
FIG. 6 is a graph illustrating hydrogen gas generation rates in water splitting and hydrogen production photocatalytic systems according to a comparative example and an example.

FIG. 6 is a graph illustrating hydrogen gas generation rates in water splitting and hydrogen production photocatalytic systems according to a comparative example and an example.

Referring to FIG. 6, it may be confirmed that when the phosphor monomolecular compound according to according to an embodiment of the present invention is used as a water oxidation photocatalyst, a higher hydrogen generation rate is obtained than that of g-CN powder.

In order to be used as an efficient photocatalyst material, a high visible light absorbance and a wide specific surface area are required to provide reaction sties where catalytic reactions may occur.

Since g-CN, which has been conventionally used as a water splitting and hydrogen production catalyst, is manufactured by firing at a temperature of 600° C. to 700° C., it is difficult to control characteristics thereof. On the contrary, the phosphor monomolecular compounds according to the present invention have high visible light absorbance as described above in Experimental Example 1. Also, due to strong intermolecular attraction, a supramolecule is easily formed, and the specific surface area may be increased by controlling the structure. By adjusting solubility of the highly water-soluble phosphor monomolecular compounds, π-π interaction between molecules may be controlled, so that a crystal structure having a large specific surface area may be formed. Thus, the monomolecular compound according to the present invention may be used as a water splitting and hydrogen production catalyst, thereby exhibiting excellent performance.

As described above, referring to Experimental Examples 1 to 3, it may be confirmed that the phosphor monomolecular compounds represented by Chemical Structural Formulae 1 to 3 above have excellent absorption spectra and high efficiency, as the organic transistors or the water splitting and hydrogen production catalysts.

While one or more embodiments of the present invention have been described with reference to the drawings, it will be understood by those of ordinary skill in the art that various changes in form and details may be made therein without departing from the spirit and scope of the present invention as defined by the following claims.

INDUSTRIAL APPLICABILITY

As described above, the water-soluble monomolecular compound including the 1,5-naphthyridine-2,6-dione structure according to the present invention may realize a wide range of wavelengths and may provide a phosphor having excellent photoluminescent efficiency, and thus the industrial applicability of the present invention may be considered high.

In addition, since performance of the organic transistor and the water splitting and hydrogen production photocatalytic system may be improved by using the monomolecular compound, the industrial applicability of the present invention may be considered high.

The invention claimed is:
1. A phosphor monomolecular compound represented by Chemical Structural Formula 1:

[Chemical Structural Formula 1]

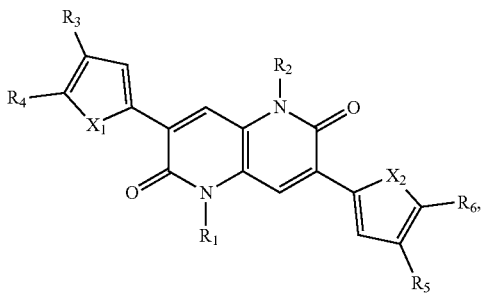

wherein:
X₁ and X₂ are each independently O, S, Se, NH, or NR';
R₁ and R₂ are each independently a C5-C14 alkyl group;
R₃, R₄, R₅, and R₆ are each independently H, F, Cl, Br, I, a C1-C50 alkyl group, a C6-C50 aryl group, —COOR', —(CH₂CH₂O)$_n$CH₃, or NR'₂; and
R's are each independently a C1-C50 alkyl group or a C6-C50 aryl group, and the n is an integer from 1 to 50.

2. The phosphor monomolecular compound of claim 1, wherein the R₃, R₄, R₅, R₆, and R' are each independently a C1-C26 alkyl group or a C6-C32 aryl group.

3. The phosphor monomolecular compound of claim 1, wherein the R₃, R₄, R₅, and R₆ are each independently a C9-C22 alkyl group.

4. An organic transistor comprising:
a substrate;
a gate electrode formed on the substrate;
an insulating layer formed on the gate electrode;
a hole transport layer formed on the insulating layer; and
a source electrode and a drain electrode formed on the hole transport layer,
wherein the hole transport layer comprises a phosphor monomolecular
compound represented by Chemical Structural Formula 1:

[Chemical Structural Formula 1]

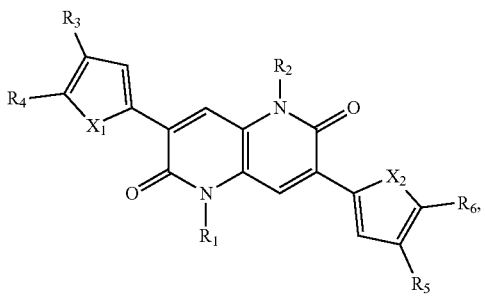

and
wherein:
X₁ and X₂ are each independently O, S, Se, NH, or NR';
R₁ and R₂ are each independently a C5-C14 alkyl group;
R₃, R₄, R₅, and R₆ are each independently H, F, Cl, Br, I, a C1-C50 alkyl group, a C6-C50 aryl group, —COOR', —(CH₂CH₂O)$_n$CH₃, or NR'₂; and
R's are each independently a C1-C50 alkyl group or a C6-C50 aryl group, and the n is an integer from 1 to 50.

5. A water splitting and hydrogen production photocatalytic system comprising a photocatalyst in an aqueous solution, wherein the photocatalyst comprises a phosphor monomolecular compound
represented by Chemical Structural Formula 1:

[Chemical Structural Formula 1]

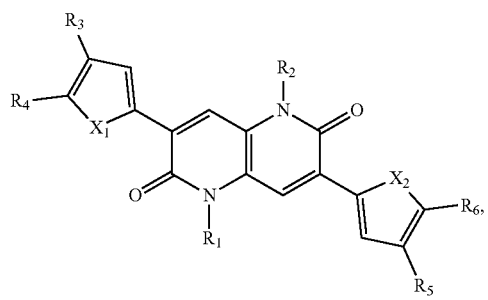

and
wherein:
X₁ and X₂ are each independently O, S, Se, NH, or NR';
R₁ and R₂ are each independently a C5-C14 alkyl group;
R₃, R₄, R₅, and R₆ are each independently H, F, Cl, Br, I, a C1-C50 alkyl group, a C6-C50 aryl group, —COOR', —(CH₂CH₂O)$_n$CH₃, or NR'2; and
the R's are each independently a C1-C50 alkyl group or a C6-C50 aryl group, and the n is an integer from 1 to 50.

6. The organic transistor of claim 4, wherein the R₃, R₄, R₅, R₆, and R' are each independently a C1-C26 alkyl group or a C6-C32 aryl group.

7. The organic transistor of claim 4, wherein the R₃, R₄, R₅, and R₆ are each independently a C9-C22 alkyl group.

8. The water splitting and hydrogen production photocatalytic system of claim 5, wherein the R₃, R₄, R₅, R₆, and R' are each independently a C1-C26 alkyl group or a C6-C32 aryl group.

9. The water splitting and hydrogen production photocatalytic system of claim 5, wherein the R₃, R₄, R₅, and R₆ are each independently a C9-C22 alkyl group.

* * * * *